(12) United States Patent
Sharpe et al.

(10) Patent No.: US 10,197,493 B2
(45) Date of Patent: Feb. 5, 2019

(54) MULTIPLE FLOW CHANNEL PARTICLE ANALYSIS SYSTEM

(71) Applicant: CYTONOME/ST, LLC, Boston, MA (US)

(72) Inventors: Johnathan Charles Sharpe, Hamilton (NZ); Emanuel Tito Mendes Machado, Merrimack, NH (US); Blair D. Morad, Ipswich, MA (US); Rudolf Hulspas, Maynard, MA (US); Donald Francis Perrault, Jr., Brighton, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 0 days.

(21) Appl. No.: 15/483,309

(22) Filed: Apr. 10, 2017

(65) Prior Publication Data
US 2017/0343467 A1 Nov. 30, 2017

Related U.S. Application Data

(63) Continuation of application No. 14/739,812, filed on Jun. 15, 2015, now Pat. No. 9,618,442, which is a
(Continued)

(51) Int. Cl.
*G01N 21/64* (2006.01)
*G01N 15/14* (2006.01)
(Continued)

(52) U.S. Cl.
CPC ..... *G01N 15/1484* (2013.01); *G01N 15/1012* (2013.01); *G01N 15/1429* (2013.01);
(Continued)

(58) Field of Classification Search
CPC .......... G01N 15/1484; G01N 15/1012; G01N 15/1429; G01N 15/1459; G01N 15/1056; G01N 21/53; G01N 21/64
See application file for complete search history.

(56) References Cited

U.S. PATENT DOCUMENTS 7,492,522 B2 * 2/2009 Gilbert ............... G01N 21/6452
356/338
8,154,724 B2 4/2012 Mitchell et al.
(Continued)

FOREIGN PATENT DOCUMENTS

WO 2004088283 10/2004
WO 2004088283 A2 10/2004
(Continued)

OTHER PUBLICATIONS

Exam Report dated Oct. 10, 2015 in related European Patent Application No. 11707946.7, 5 pages.
(Continued)

*Primary Examiner* — Michael P Stafira
(74) *Attorney, Agent, or Firm* — McCarter & English, LLP; David R. Burns

(57) ABSTRACT

A microfluidic multiple channel particle analysis system which allows particles from a plurality of particle sources to be independently simultaneously entrained in a corresponding plurality of fluid streams for analysis and sorting into particle subpopulations based upon one or more particle characteristics.

12 Claims, 18 Drawing Sheets

Related U.S. Application Data continuation of application No. 13/577,216, filed as application No. PCT/US2011/000211 on Feb. 4, 2011, now Pat. No. 9,057,676.

(60) Provisional application No. 61/337,581, filed on Feb. 5, 2010.

(51) Int. Cl.
*G01N 15/10* (2006.01)
*G01N 21/53* (2006.01)

(52) U.S. Cl.
CPC ......... *G01N 15/1459* (2013.01); *G01N 21/53* (2013.01); *G01N 21/64* (2013.01); *G01N 15/1056* (2013.01); *G01N 2015/1018* (2013.01); *G01N 2015/1075* (2013.01); *G01N 2015/1402* (2013.01); *G01N 2015/149* (2013.01)

(56) References Cited

U.S. PATENT DOCUMENTS

| | | | |
|---|---|---|---|
| 8,731,860 | B2 | 5/2014 | Charles et al. |
| 2005/0112541 | A1 | 5/2005 | Durack et al. |
| 2006/0244964 | A1 | 11/2006 | Cox et al. |
| 2008/0087068 | A1 | 4/2008 | Roth et al. |
| 2008/0108146 | A1 | 5/2008 | Jiang |
| 2008/0145286 | A1 | 6/2008 | Maltezos et al. |
| 2009/0109436 | A1 | 4/2009 | Shinoda |
| 2010/0220321 | A1 | 9/2010 | Kao et al. |
| 2011/0069311 | A1 | 3/2011 | Takeda |
| 2013/0016335 | A1 | 1/2013 | Lo et al. |
| 2013/0080082 | A1 | 3/2013 | Howes et al. |
| 2013/0334407 | A1 | 12/2013 | Perrault, Jr. et al. |
| 2014/0273067 | A1 | 9/2014 | Wanders et al. |
| 2014/0273192 | A1 | 9/2014 | Sharpe et al. |
| 2015/0233704 | A1 | 8/2015 | Martini et al. |

FOREIGN PATENT DOCUMENTS

| | | |
|---|---|---|
| WO | 2009146036 | 12/2009 |
| WO | 2009146036 A2 | 12/2009 |

OTHER PUBLICATIONS

U.S. Appl. No. 13/022,525, filed Feb. 7, 2011, Patented.
U.S. Appl. No. 13/577,216, filed Aug. 3, 2012, Patented.
U.S. Appl. No. 14/281,353, filed May 19, 2014, Pending.
U.S. Appl. No. 14/739,812, filed Jun. 15, 2015, Granted.
Communication pursuant to Article 94(3) EPC issued in European Patent Application No. 11707946.7, dated Nov. 13, 2014.
International PCT Patent Application No. PCT/US2011/000211, filed Feb. 4, 2011.
International Preliminary Report on Patentability and Written Opinion for International Application No. PCT/US2011/000211 dated Aug. 7, 2012.
International Preliminary Report on Patentability and Written Opinion for International Application No. PCT/US2011/023945 dated Aug. 7, 2012.
International Search Report and Written Opinion in PCT/US2011/023945, dated Jul. 29, 2011.
International Search Report for International Application No. PCT/US2011/000211 dated Apr. 14, 2011.
International Search Report for International Application No. PCT/US2011/023945 dated Jul. 29, 2011.
Invitation to Pay Additional Fees and, Where Applicable, Protest Fees in PCT/US2011/023945, dated Jun. 6, 2011.
U.S. Appl. No. 61/337,581, filed Feb. 5, 2010.

\* cited by examiner

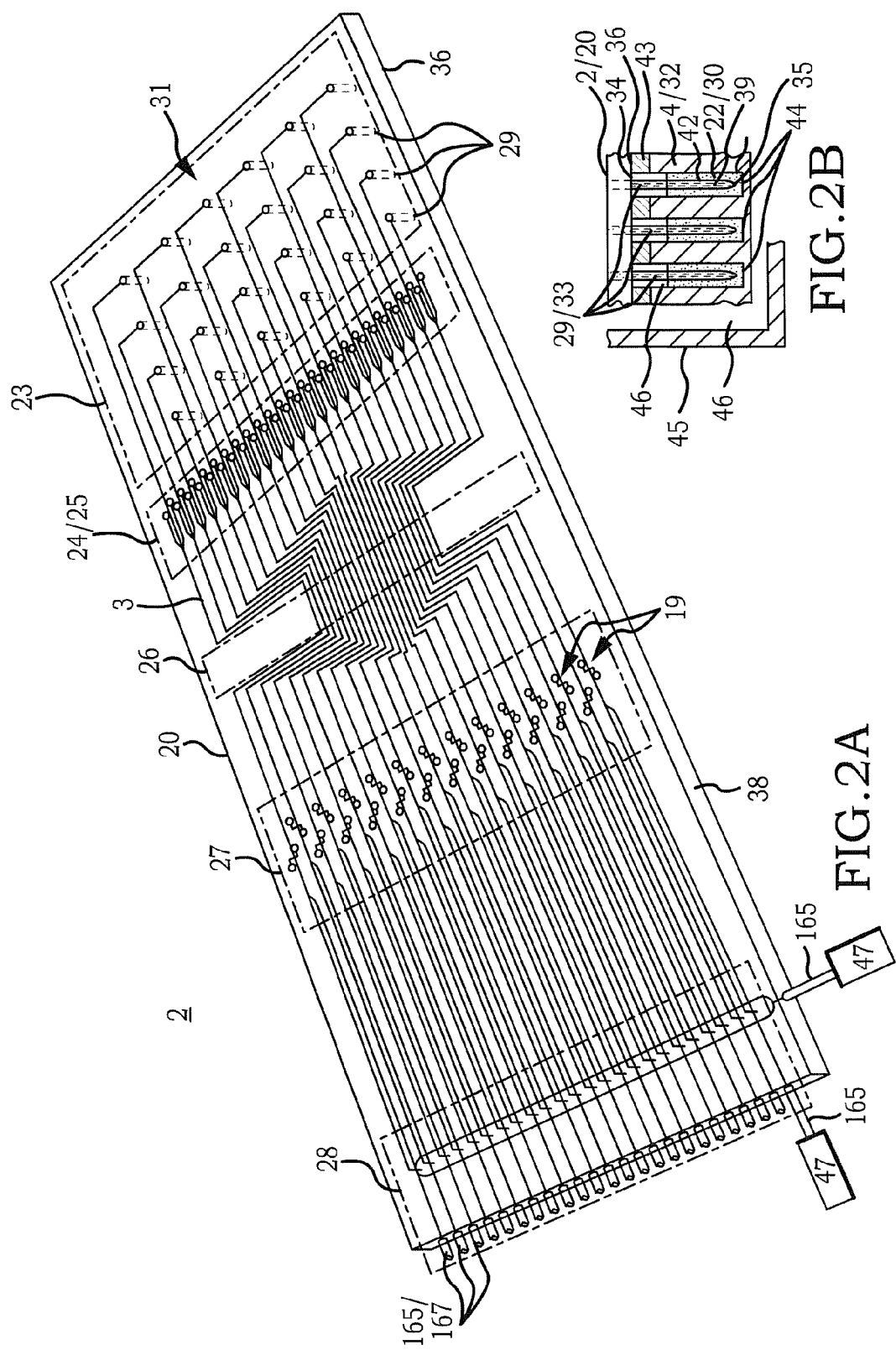

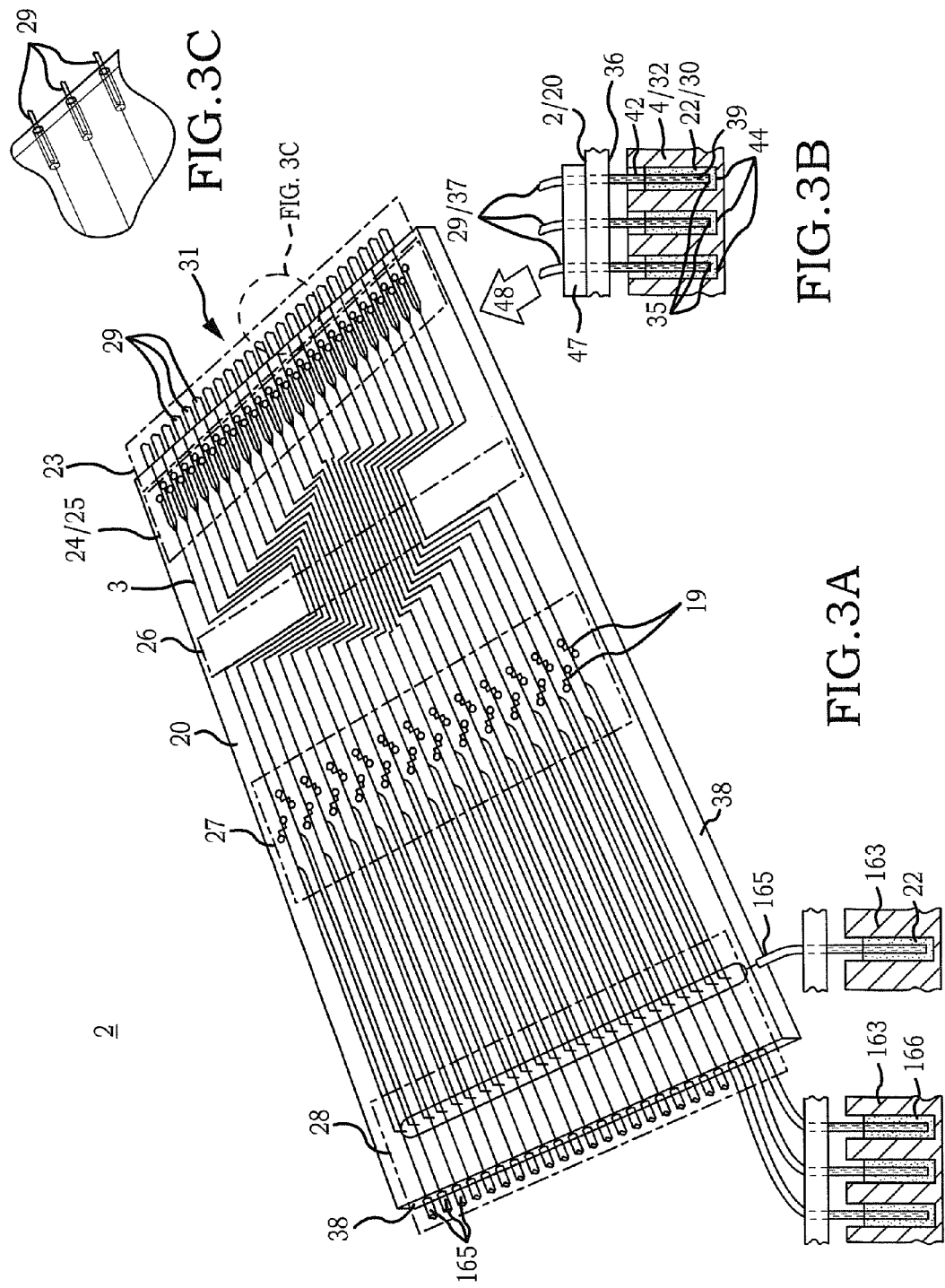

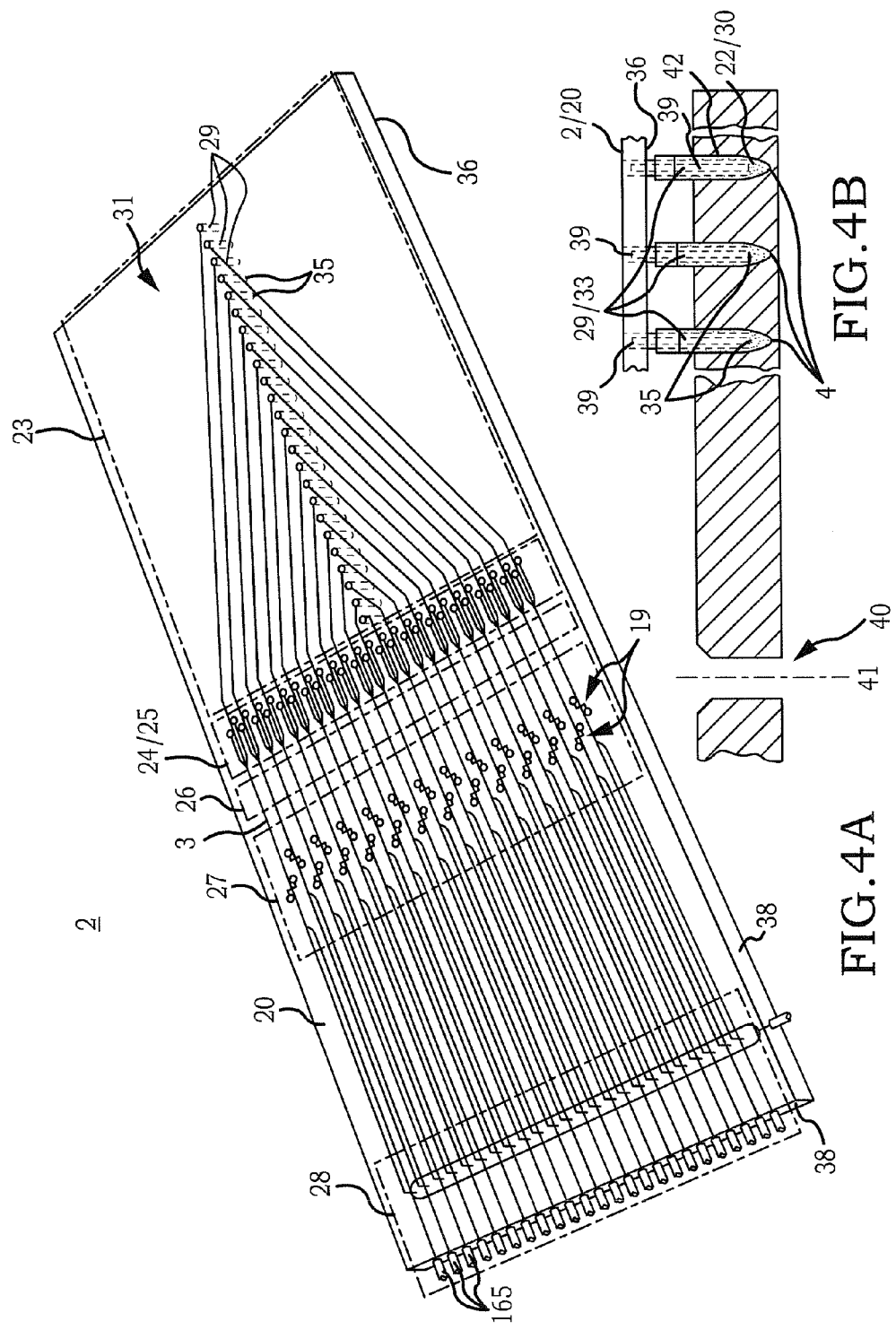

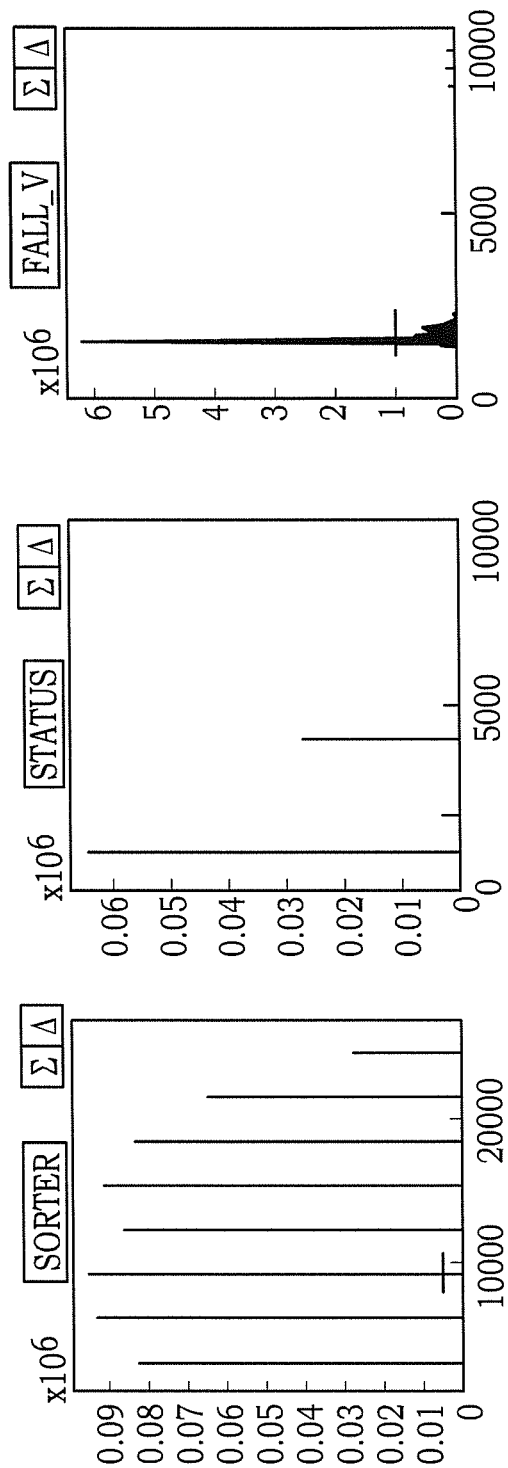

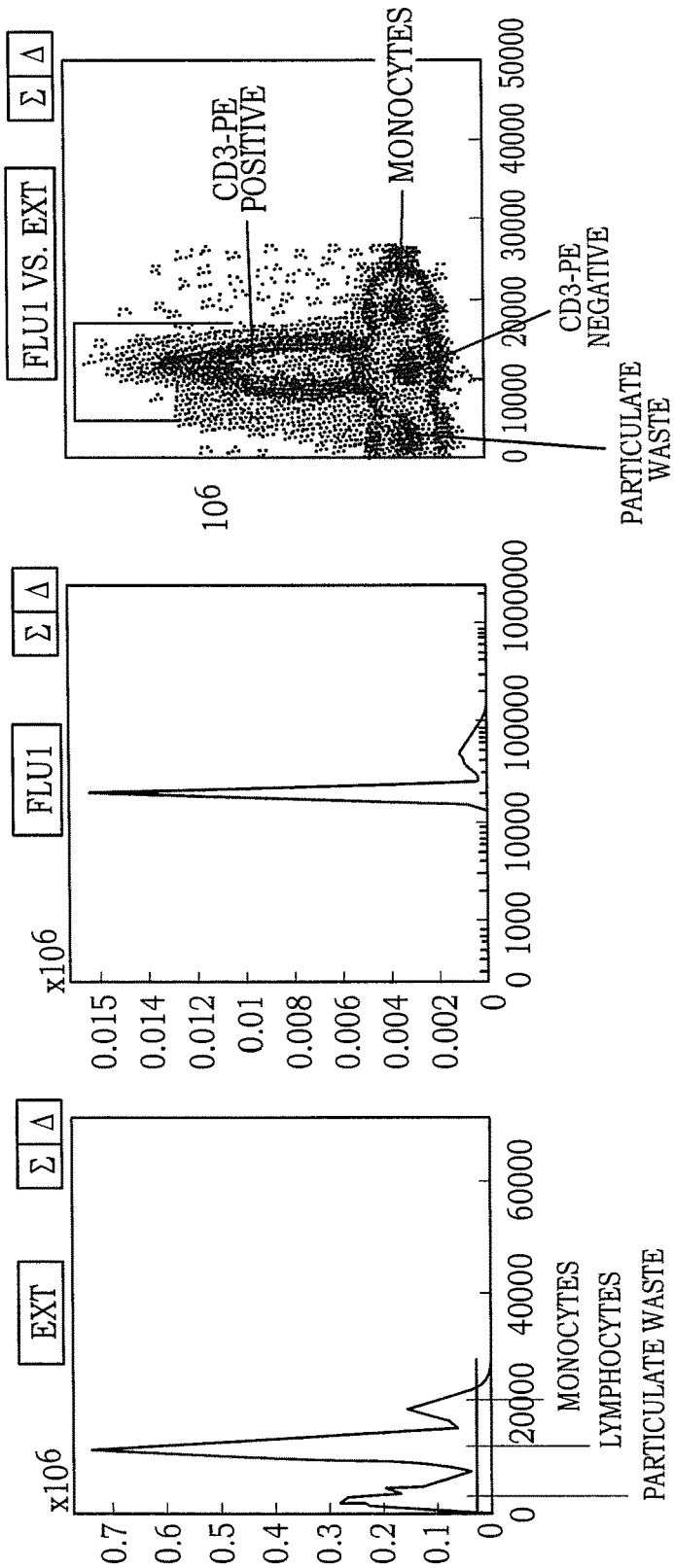

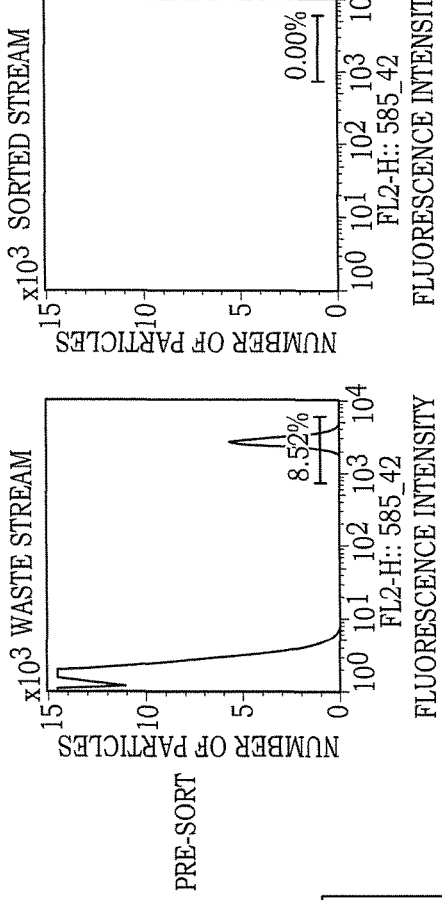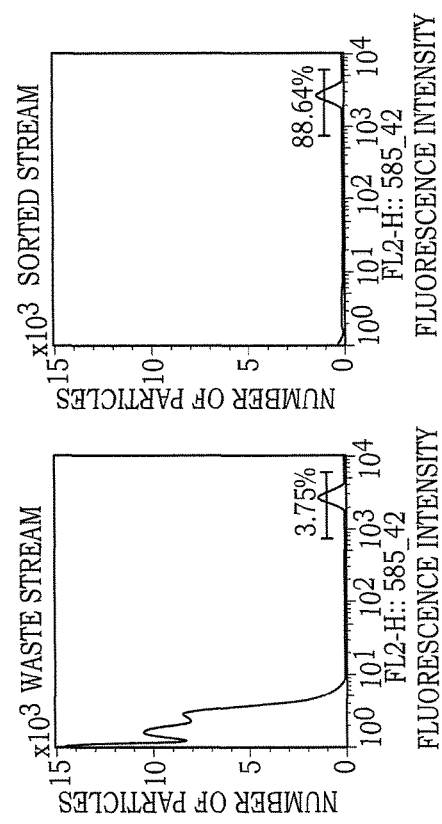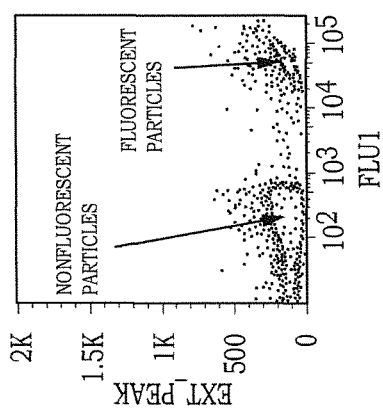

MULTIPLE FLOW CHANNEL PARTICLE ANALYSIS SYSTEM

RELATED APPLICATIONS

This application is a Continuation of U.S. patent application Ser. No. 14/739,812, filed Jun. 15, 2015, entitled "Multiple Flow Channel Particle Analysis System," which is a Continuation of U.S. patent application Ser. No. 13/577,216 filed Aug. 3, 2012, entitled "Multiple Flow Channel Particle Analysis System", which, in turn, is a 35 U.S.C. § 371 United States National Stage application of International Patent Corporation Treaty Patent Application No. PCT/US2011/000211, filed Feb. 4, 2011, which claims the benefit of U.S. Provisional Patent Application No. 61/337,581, filed Feb. 5, 2010, the contents of each identified application are hereby expressly incorporated by reference in their entirety.

I. TECHNICAL FIELD

A microfluidic multiple flow channel particle analysis system which provides a microfluidic chip having a plurality of flow channels each having one or more optical windows which admit an amount of light and a plurality of detectors adapted to generate a corresponding plurality of signals which vary based upon the amount of light passing through or emitted from each of the plurality of flow channels and an analyzer adapted to concurrently analyze a plurality of signals from said plurality of detectors in relation to executable particle analysis processing steps to convert said plurality of signals into data for each of said plurality of flow channels.

II. BACKGROUND

Conventional flow cytometry is a technique which allows for the analysis, counting, and sorting of microscopic particles into subpopulations based on one or more particle characteristics. Typically, a beam of light of a single wavelength is directed onto a hydrodynamically-focused stream of fluid. A number of detectors are aimed at the point where the stream passes through the light beam: one in line with the light beam (forward scatter or FSC) and one or more perpendicular to it (side scatter or SSC) and one or more fluorescent detectors. Each particle entrained in the stream of fluid passing through the beam scatters the light in some way, and fluorescent substances found (either intrinsic or added) in the particle or attached to the particle may be excited into emitting light at a longer wavelength than the light source. This combination of scattered and fluorescent light is received by the detectors, and, by analyzing fluctuations in brightness at each detector, it is then possible to derive various types of information about the physical and chemical structure of each individual particle. FSC typically correlates with the cell size and SSC typically correlates with inner complexity or morphology of the particle (for example shape of the nucleus, the amount and type of cytoplasmic granules or the membrane roughness, or the like).

In particular, the configuration of the flow cell of conventional flow cytometers support a single fluid stream in which particles align to pass in single file through the light beam for interrogation. Because conventional flow cytometers produce only a single fluid stream, the number of particles which can pass through single file through the flow cytometer to be interrogated by the beam of light and associated optical system, detection or computer system can be limited during a period of time.

Additionally, conventional flow cytometers utilize a sheath fluid to hydrodynamically focus the sample fluid stream entraining particles for presentation to the beam of light. Additionally, hydrodynamic focusing to generate a laminar flow of a sample fluid stream within a sheath fluid stream to focus particles requires use of a flow cell having at least a sheath fluid flow path and sample fluid flow path each of which are reduced in diameter to force the particles to the center of the fluid stream. This approach requires a flow cell of substantially greater constructional and operational complexity than if sufficient centration, alignment and spacing of particles could be achieved within a single fluid stream without utilizing sheath fluid. Additionally, providing sheath fluid in the context of a microfluidic chip necessitates an additional fluidic interface between the sheath fluid source and the microfluidic chip.

Moreover, conventional flow cytometers do not concurrently sample particles whether of the same or different types or populations of particles from a corresponding plurality of sample sources, such as 12, 24, 48, 96, 384, or 1536 particle sources, into a corresponding plurality of sample fluid streams for concurrent analysis or separation into subpopulations. Conventional flow cytometers process sample particles in an asynchronous or non-concurrent basis through a single flow cytometry unit. In part, this may be due to the fact that different samples of particles can vary by a number of factors such as viscosity of sample fluid, concentration of particles, size of particles, motility of particles, velocity at which particles can be carried in a fluid stream, particle characteristics analyzed, relative difference in the particle characteristic(s) being analyzed or differentiated, or the like. As a result, each of a plurality of sample fluid streams entraining a corresponding plurality of different particle types or populations, can yield analyzable or sortable events which may occur asynchronously between a plurality of sample fluid streams, but must be concurrently analyzed and sorted. This does not appear to have been achieved utilizing a conventional unitary flow cytometry system. Rather, different particle samples are typically analyzed and sorted using separate flow cytometers each of which analyzes and sorts the particles in a single fluid stream with each analyzable or sortable particle event processed in independent asynchronous serial fashion.

The invention described herein addresses the problems associated with the simultaneous analysis and sorting of a plurality of different particle types in a corresponding plurality of fluid streams in which analyzable or sortable events occur either synchronously or asynchronously between each of the plurality of fluid streams entraining particles.

III. DISCLOSURE OF INVENTION

Accordingly, a broad object of the invention can be to provide embodiments of a microfluidic multiple flow channel particle analysis system which allows particles from a plurality of particle sources to be independently and simultaneously entrained in a corresponding plurality of fluid streams for analysis and sorting into particle subpopulations based upon one or more particle characteristics.

Another broad object of the invention can be to provide embodiments which allow like from a plurality of particle sources to be independently and simultaneously entrained in a corresponding plurality of fluid streams for independent and concurrent analysis and sorting into particle subpopulations based upon one or more particle characteristics.

Another broad object of the invention can be to provide embodiments which allow unlike particles with different particle characteristics from a plurality of different particle sources to be independently and simultaneously entrained in a corresponding plurality of fluid streams for independent and concurrent analysis and sorting into particle subpopulations based upon one or more particle characteristics.

Another broad object of the invention can be to provide a microfluidic multiple channel particle analysis system having a microfluidic chip having a plurality of flow channels each configured to entrain particles in a fluid stream with sufficient centration, alignment, and spacing in relation to the corresponding channel to allow analysis and sorting of each particle without the use of a sheath fluid and without the use of conventional laminar flow in which a sample fluid stream flows substantially co-axially within a sheath fluid stream.

Another broad object of the invention can be to provide a microfluidic multiple flow channel particle analysis system having a microfluidic chip having a plurality of flow channels each of the plurality of flow channels interrogated, and the resulting optical extinction, scatter and fluorescence analyzed, using common interrogation, optics and data processing subsystems.

Another broad object of the invention can be to provide a microfluidic multiple flow channel particle analysis system having a microfluidic chip having a plurality of flow channels each correspondingly enclosing a fluid stream entraining a plurality of particles which can be received from a plurality of sealed sample sources and can be delivered to a plurality of sealed sample collection containers to provide in part or in whole a closed particle analysis and particle sorting system.

Naturally, further objects of the invention are disclosed throughout other areas of the specification, drawings, photographs, and claims.

IV. BRIEF DESCRIPTION OF THE DRAWINGS

FIG. 2A is a perspective view of a particular embodiment of a multiple flow channel microfluidic chip.

FIG. 2B is a cross sectional view of a particular embodiment of a multiple welled sample source each well containing sample fluid entraining a plurality of particles each well fluidicly coupled to a corresponding inlet element of the microfluidic chip shown in FIG. 2A.

FIG. 3A is a perspective view of a second particular embodiment of a multiple flow channel microfluidic chip.

FIG. 3B is a cross sectional view of a particular embodiment of a multiple welled sample source each well containing sample fluid entraining a plurality of particles each well fluidicly coupled to a corresponding inlet element of the microfluidic chip shown in FIG. 3A.

FIG. 3C is a detail view of a plurality of inlet elements of the second particular embodiment of the multiple flow channel microfluidic chip depicted in FIG. 3A.

FIG. 4A is a perspective view of a third particular embodiment of a multiple flow channel microfluidic chip.

FIG. 4B is a cross sectional view of a particular embodiment of plurality of sample sources each sample source containing sample fluid entraining a plurality of particles each sample source fluidicly coupled to a corresponding inlet element of the microfluidic chip shown in FIG. 4A.

FIG. 14A is a plot of live blood cells labeled with PE-conjugated anti-CD3 antibody, interrogated per second for each of eight flow channels of a microfluidic chip in accordance with an embodiment of the invention.

FIG. 14B is a plot of live blood cells labeled with PE-conjugated anti-CD3 antibody, in all eight flow channels of the microfluidic chip of FIG. 19A which meet the threshold criteria to be characterized as an event for further analysis and sorting in accordance with an embodiment of the invention.

FIG. 14C is a plot of the velocity of live blood cells in all eight flow channels of the microfluidic chip of FIG. 19A in accordance with an embodiment of the invention.

FIG. 14D is a plot of the optical extinction of live blood cells gated to separate the optical extinction for lymphocytes, monocytes and particulate waste in all eight flow channels of the microfluidic chip of FIG. 19A in accordance with an embodiment of the invention.

FIG. 14E is a plot of the total emitted fluorescence of live blood cells labeled with PE-conjugated anti-CD3 antibody to separate the fluorescence intensities for anti-CD3 labeled cells and cells that are not labeled with anti-CD3 in all eight flow channels of the microfluidic chip of FIG. 19A in accordance with an embodiment of the invention.

FIG. 14F is a two-dimensional scatter plot of the optical fluorescence of live blood cells gated to separate the emitted fluorescence for CD-3-PE positive lymphocytes, CD-3-PE negative lymphocytes, monocytes, and particulate waste in all eight flow channels of the microfluidic chip of FIG. 19A in accordance with an embodiment of the invention.

FIG. 22 is a bivariate plot which shows the combined data of concurrent analysis of a mixture of non-fluorescent particles (approximately 90%) and fluorescent particles (approximately 10%) particles in a plurality of flow channels of an embodiment of a microfluidic chip such as shown in FIG. 5A.

FIG. 23 is a histogram which plots for a pre-sort process the number of particles in relation to fluorescence intensity of the mixture of non-fluorescent particles and fluorescent particles in a plurality of flow channels of an embodiment of a microfluidic chip used in FIG. 22 in the waste stream.

FIG. 24 is a histogram which plots for a pre-sort process the number of particles in relation to fluorescence intensity of the mixture of non-fluorescent particles and fluorescent particles in a plurality of flow channels of an embodiment of a microfluidic chip used in FIG. 22 in the sorted stream.

FIG. 25 is a histogram which plots during a sorting process the number of particles in relation to fluorescence intensity of the mixture of non-fluorescent particles and fluorescent particles in a plurality of flow channels of an embodiment of a microfluidic chip used in FIG. 22 in the waste stream.

FIG. 26 is a histogram which plots during a sorting process the number of particles in relation to fluorescence intensity of the mixture of non-fluorescent particles and fluorescent particles in a plurality of flow channels of an embodiment of a microfluidic chip used in FIG. 22 in the sorted stream.

V. MODE(S) FOR CARRYING OUT THE INVENTION

Figure 1:
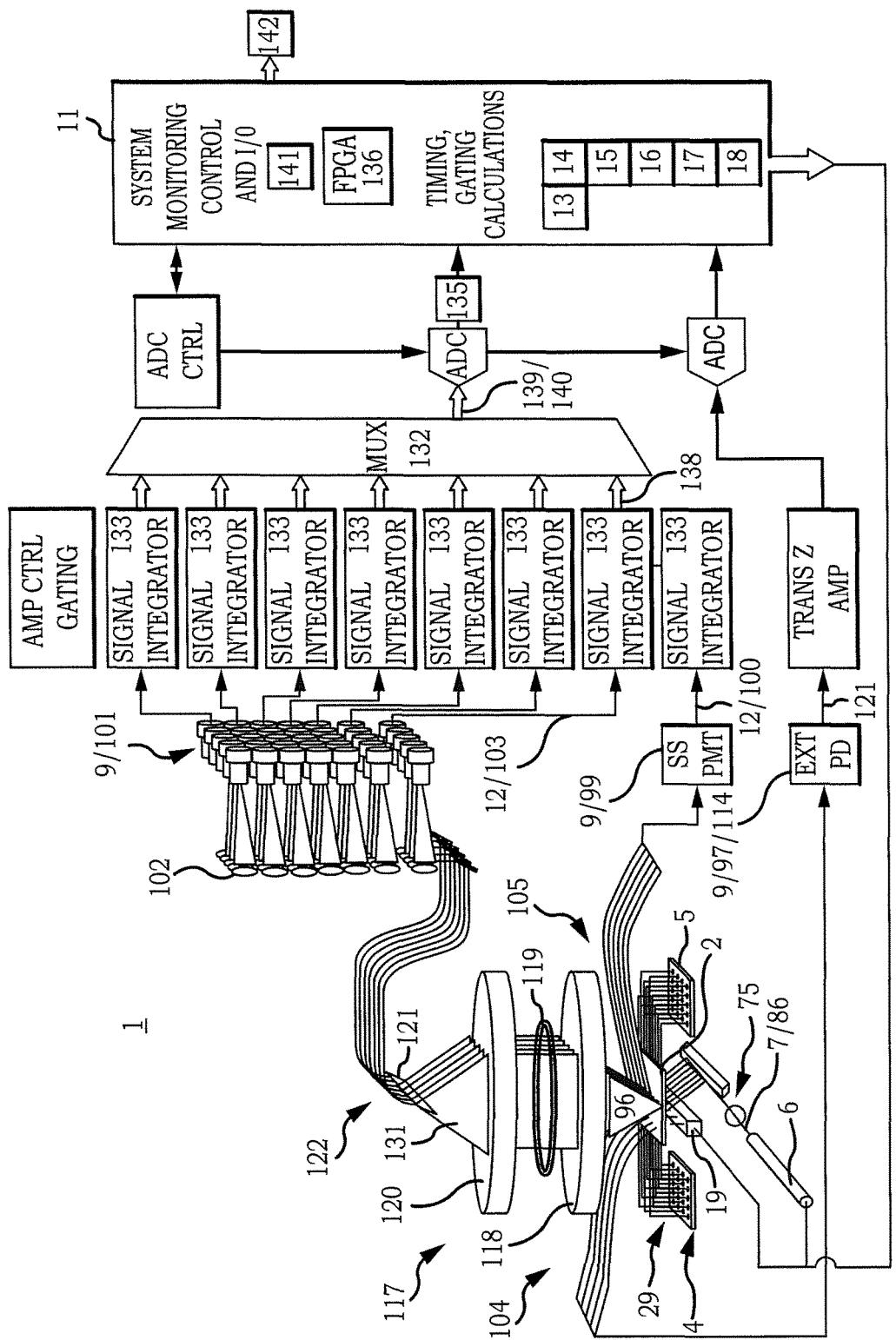
FIG. 1 is a block diagram of a particular embodiment of a multiple flow channel particle analysis and sorting system.

Referring primarily to FIG. 1, which provides a general overview of an inventive microfluidic multiple flow channel particle analysis system (1). The microfluidic multiple flow channel particle analysis system (1) can provide a microfluidic chip (2) having a plurality of flow channels (3) each fluidicly coupled between at least one sample source (4) and further to at least one collection container (5). A light source (6) can be adapted to locate a beam of light (7) incident an optical window (8) in each of the plurality of flow channels (3) of the microfluidic chip (2). A plurality of detectors (9) can be adapted to receive an amount of light (10) passing through or emitted from each of the plurality of flow channels (3) of the microfluidic chip (2). An analyzer (11) can be adapted to concurrently analyze a plurality of signals (12) from the plurality of detectors (9) in relation to gated criteria (13) for each optical window (8) to distinguish threshold events (14) which occur in each of the plurality of flow channels (3). The analyzer (11) can be further adapted to concurrently analyze the plurality of signals (12) corresponding to the threshold events (14) in relation to executable particle analysis processing steps (15) to transform the plurality of signals (12) related to threshold events (14) occurring in each of the plurality of flow channels (3) into threshold event data units (16). The analyzer (11) can be further adapted to concurrently differentiate between the threshold event data units (16) in relation to executable particle separation processing steps (17) to convert the threshold event data units (16) to timed events (18) which allow operation of a particle sorter (19) associated with each of the plurality of flow channels (3).

Now referring primarily to FIGS. 2A and 2B, 3A and 3B, 4A and 4B, and 5A and 5B each of which illustrate a particular non-limiting embodiment of a microfluidic chip (2) having a plurality of flow channels (3) disposed in a substrate material (20) each of the flow channels (3) adapted to convey a corresponding one of a plurality of sample fluid streams (21) each of which can entrain a plurality of particles (22) from at least one sample source (4).

As used herein, the term "substrate material" refers to any material in which one or more flow channels (3) can be disposed and which is compatible with each of a plurality of sample fluid streams (21) and the plurality of particles (22) entrained in each of the plurality of sample fluid streams (21) such as a polymeric material, plastic, glass, ultra-violet fused silica, borofloat glass, metal, crystalline, or the like, or combinations thereof. The substrate material can comprise a single layer or multiple layers depending on the manner of fabrication of the microfluidic chip (2) or of the plurality of flow channel(s) (3) disposed therein.

Figures 5A, 5B:
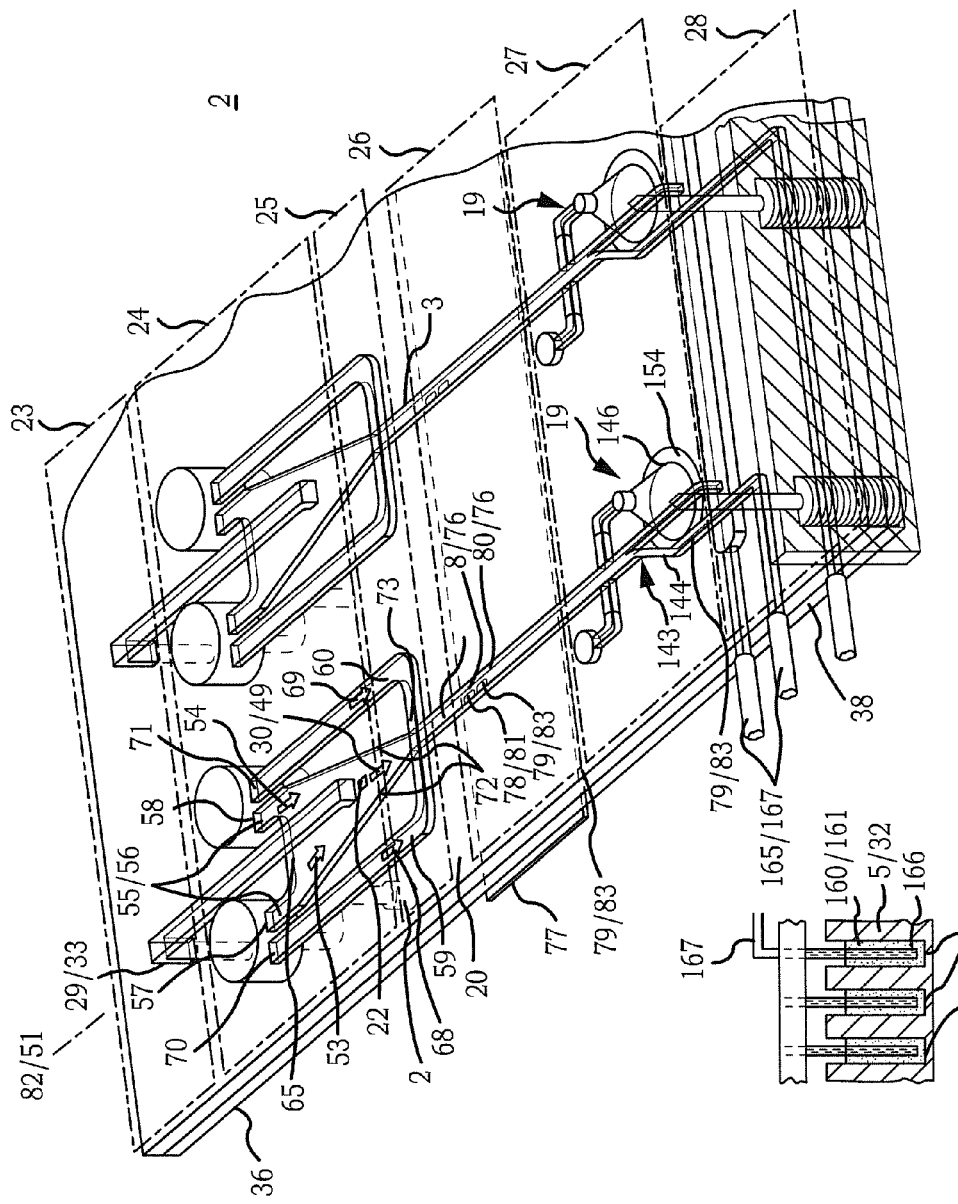
FIG. 5A is a perspective view of a particular embodiment of a flow channel disposed in a particular embodiment of a multiple flow channel microfluidic chip.
FIG. 5B is a cross section view of a particular embodiment of a multiple welled collection container fluidicly coupled with the embodiment of multiple flow channel microfluidic chip shown in FIG. 5A.
Figure 11:
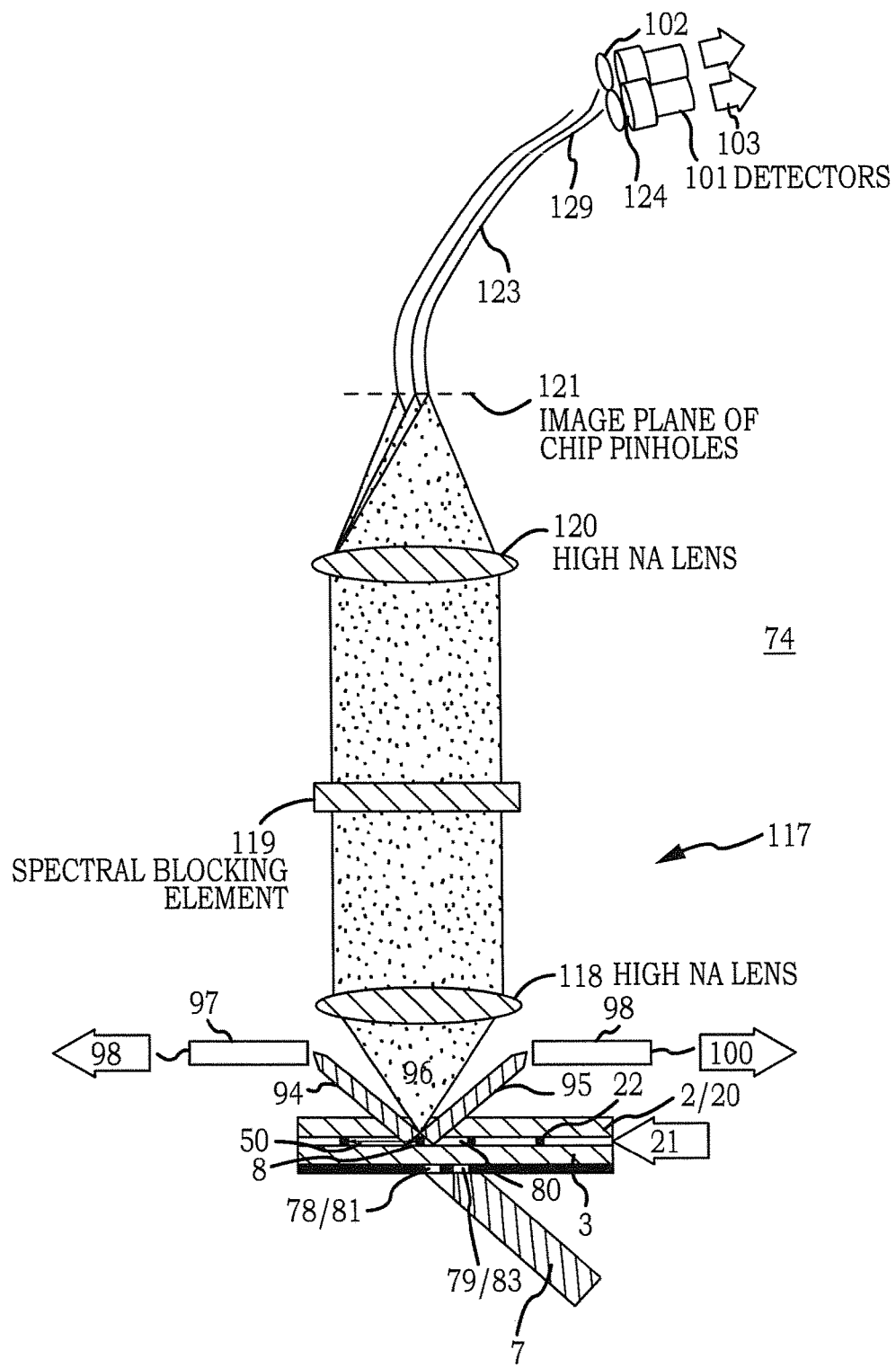
FIG. 11 is a cross-sectional view of a particular embodiment of an optical detection system for the detection of light extinction, side scatter and emitted light in a plurality of flow channels of multiple flow channel microfluidic chips such as those shown in FIGS. 2A, 3A, 4A and 5A.

The term "flow channel" or "plurality of flow channels" as used herein refers to one or more pathway(s) formed in or through a substrate material (20) of a microfluidic chip (2) that allows for movement of fluids, such as liquids or gases therein. While the Figures (see for example FIGS. 5A and 11 show each of the plurality of flow channels (3) as being generally rectangular in transverse cross-section; the invention is not so limited, and each of the plurality of flow channels (3) can have any cross-sectional configuration capable of allowing for movement of fluids, such as circular, oval, square, triangle, trapezoid, U-shaped, or the like. While particular embodiments can have cross-sectional dimensions in the range of between about 1.0 micrometer ("μm") and about 500 μm, or between about 25 μm and about 350 μm, or between about 50 μm and about 300 μm and within each range embodiments can vary in increments of 1 μm; the invention is not so limited, and one of ordinary skill in the art in view of the description and figures can determine an appropriate cross sectional configuration of the flow channel in relation to a particular application.

Each of the plurality of flow channels (3) disposed within the microfluidic chip (2) can have any of a numerous and varied arrangements. As non-limiting examples, the arrangement of the flow channels (3) in a microfluidic chip (2) can be generally linear as shown in FIG. 4A, or can be a non-linear arrangement as shown for example in FIGS. 2A and 3A. Each microfluidic chip (2) can include a suitable plurality of channels (3). While FIGS. 2A, 3A, and 4A each show embodiments of the invention, which include a microfluidic chip (2) having twenty four channels; the invention is not so limited, and embodiments of the invention can include a lesser or greater plurality of flow channels (3) depending upon the application such as eight, twelve, sixteen, twenty-four, forty-eight, seventy-two, ninety-six, three hundred and eighty four, fifteen hundred and thirty six, or the like. Additionally, one or more microfluidic chips (2) can be utilized separately or together to provide a lesser or greater plurality of flow channels (3).

As to other embodiments of the invention, the plurality of flow channels (3) can be selected from the group consisting of between: 2 flow channels and 5 flow channels, between 2 flow channels and 10 flow channels between 5 flow channels and 15 flow channels, between 10 flow channels and 20 flow channels, between 15 flow channels and 25 flow channels, between 20 flow channels and 30 flow channels, between 25 flow channels and 35 flow channels, between 30 flow channels and 40 flow channels, between 35 flow channels and 45 flow channels, between 40 flow channels and 50 flow channels, between 45 flow channels and 55 flow channels, between 50 flow channels and 60 flow channels, between 55 flow channels and 65 flow channels, between 60 and 70 flow channels, between 65 flow channels and 75 flow channels, between 70 flow channels and 80 flow channels, between 75 flow channels and 85 flow channels, between 80 flow channels and 90 flow channels, between 85 flow channels and 95 flow channels, between 90 flow channels and 100 flow channels, between 95 flow channels and 105 flow channels, between 100 flow channels and 110 flow channels, between 105 flow channels and 115 flow channels, between 110 flow channels and 120 flow channels, between 115 flow channels and 125 flow channels, between 120 flow channels and 130 flow channels, between 125 flow channels and 135 flow channels, between 135 flow channels and 145 flow channels, between 140 flow channels and 150 flow channels, between 145 flow channels and 155 flow channels, between 150 flow channels and 160 flow channels, between 150 flow channels and 160 flow channels, between 155 flow channels and 165 flow channels, between 160 flow channels and 170 flow channels, between 165 flow channels and 175 flow channels, between 170 flow channels and 180 flow channels, between 185 flow channels and 195 flow channels, between 190 flow channels and 200 flow channels, and in similar increments up to about 1,530 flow channels, and combinations thereof.

The term "sample fluid stream" or "plurality of sample fluid streams" as used herein refers to any suitable liquid or gas (or suitable combinations or mixture of liquids or gases) compatible with the substrate material (20) and able to flow within a particular configuration of one or more flow channel(s)(3) and further compatible with the one or more particles (22) entrained therein. As one non-limiting example, the sample fluid stream (21) can comprise any of the numerous and varied sample fluids utilized in conventional preparation, analysis or sorting of a plurality of particles (22) by conventional flow cytometry, such as buffered solutions, sheath fluids, water, or the like, or combinations thereof.

As used herein, the term "particle" or "plurality of particles" refers to non-biological particles (such as polystyrene beads, magnetic beads, silica particles, or the like) which may have substantially similar or substantially dissimilar dimension; or biological particles (such as cells, stem cells, sperm cells, bacteria, viruses, fungi, yeast, bacteriophages, dissociated tissue, or the like); or such non-biological or biological particles modified with one or more ligands, labels, or fluorescent dyes, or the like; deoxyribonucleic acid ("DNA"), ribonucleic acid ("RNA"), chromosomes, oligonucleotides, proteins, peptides, antibodies, organelles, or fragments thereof whether or not bound to or associated with other non-biological particles or biological particles; and generally without limitation to the forgoing non-biological particles and biological particles and combinations thereof capable of being analyzed by embodiments of the invention or analyzed by conventional flow cytometry, and combinations thereof.

Now referring primarily to FIGS. 2A, 3A, 4A and 5A, embodiments of the invention can include a plurality of flow channels (3) disposed in a microfluidic chip (2) having one or more of an inlet region (23), a primary focusing region (24), a secondary focusing region (25), a detection region (26), a particle selection region (27), and a collection region (28). Reference to the fluidic microchip (2) having one or more of such regions referring collectively to such one more regions of the plurality of flow channels (3) within the microfluidic chip (2).

The inlet region (23) of each of a plurality of flow channels (3) can be fluidicly coupled to a corresponding one of a plurality of inlet elements (29). The plurality of inlet elements (29) can be fluidicly coupled with at least one sample source (4). As used herein the term "sample source" refers to a vessel which defines a volume capable of containing an amount of sample fluid (30) such as vials, tubes, wells, wells of a welled plate, multiple welled plates, or the like. As to particular embodiments, the plurality of inlet elements (29) can all be fluidicly coupled to one sample source (4) and as to other embodiments, each one of the plurality of inlet elements (29) can be fluidicly coupled to a corresponding one of a plurality of sample sources (4). Accordingly, as to particular embodiments, the sample fluid (30) (whether or not entraining, containing or having suspended therein a plurality of particles (22)) of one sample source (4) can be delivered through the plurality of inlet elements (29) to each one, a portion, or all of the plurality of flow channels (3) in a microfluid chip (2). As to other particular embodiments, the sample fluid (30) in each of a plurality of sample sources (4) can be delivered through a corresponding one of a plurality of inlet elements (29) to the inlet region (23) of a corresponding one of the plurality of flow channels (3) in a microfluidic chip (2).

The plurality of inlet elements (29) can further be disposed in an inlet element pattern (31). The inlet element pattern (31) allows each of the plurality of inlet elements (28) to be readily fluidicly coupled with the sample fluid (30) contained within one, more than one, or a corresponding plurality of sample sources (4).

Now referring primarily to FIGS. 2A and 2B, a particular non-limiting embodiment of the inlet region (23) of a microfluidic chip (2) can provide a plurality of inlet elements (29) in an inlet element pattern (31) of spaced columns and rows which allows fluidic coupling of each of the inlet elements (29) with the a corresponding plurality of particle sources (4) spaced in a similar array of columns and rows. While FIG. 2A shows an inlet element pattern (31) for fluidic coupling of twenty four sample sources (4) having the constructional form of a welled plate (32) arranged in six columns with four rows; the invention is not so limited, and embodiments of the inlet region (23) can provide inlet element patterns (31) configured to couple with welled plates (32) having 6 wells, 12 wells, 24 wells, 48 wells, 96 wells, 384 wells, or 1536 wells, or the like. As one non-limiting example, the welled plate (32) can be a conventional multiple welled plate.

As to this form of inlet element pattern (31), each of the plurality of inlet elements (29) can provide a substantially rigid conduit (33) having a length disposed between a pair of ends (34)(35). The length of the rigid conduit (33) can be sufficient upon fluidically coupling of a first of the pair of ends (34) at a location on a bottom surface (36) of the microfluidic chip to removably insert a second of the pair of ends (35) into one of the plurality of sample sources (4).

Now referring primarily to FIGS. 3A, 3B and 3C, another particular embodiment of the inlet element pattern (31) fluidically couples each one of the plurality of inlet elements (29) to a corresponding one of the plurality of flow channel (s) in the form of a flexible conduit (37). As one non-limiting example, each flow channel (3) can be configured to insertingly receive a first end (34) of one of the plurality of inlet elements (29) at a side (38) of the microfluidic chip (2) allowing the passage (39) within the inlet element (29) to fluidically couple with the flow channel (3) at the inlet region (23) of the flow channel (3). The second end (35) of each flexible conduit (37) can be fluidically coupled with one of the plurality of sample sources (4)(or at least one particle source (4)). As to certain embodiments, the second end (35) of the flexible conduit (37) can be coupled to any of the numerous and varied conventional autosamplers which can operate to transfer liquids from tubes, vials or welled plates.

Now referring primarily to FIGS. 4A and 4B, a particular embodiment of the inlet element pattern (31) provides a plurality of inlet elements (29)(whether rigid or flexible) spaced a distance apart in linear relation which allows fluidic coupling of each of the plurality of inlet elements (29) with a corresponding plurality of sample sources (4) spaced a distance apart in similar linear relation to the plurality of inlet elements (29).

A plurality of linear arrays each having a plurality of sample sources (4) can be disposed in radial symmetry extending outward about a central hub (40)(for example, the central hub of a carriage of an autosampler). Rotation about the axis (41) of the central hub (40) can align each of the linear arrays having a plurality of particle sources (4) with the corresponding inlet element pattern (31) in the form a linear array of a plurality of inlet elements (29). Each of the plurality of inlet elements (29) can extend from the bottom side (36) of the microfluidic chip (2) a sufficient distance to allow location of each inlet element end (35) proximate the bottom of a corresponding one of the plurality of sample sources (4).

Each of the above-described embodiments of the inlet elements (29) can have an external surface (42) which can be variously configured to insert within a particular configuration of sample source (4). A suitably configured inlet element (29) allows for removable insertion within a corresponding sample source (4) sufficient for the delivery of at least a portion of the amount of sample fluid (30) contained within the sample source (4). The amount of sample fluid (30)(whether or not containing a plurality of particles (22)) can be delivered through the inlet element (29) to the inlet region (23) of the a flow channel (3).

Now referring primarily to FIGS. 2A and 2B, transfer of the sample fluid (30) (whether not containing a plurality of particles (22)) from a sample source (4) to the inlet region (23) of a flow channel (3) as a sample fluid stream (21) can be achieved in numerous and varied ways. As a non-limiting example, a particle source (4) can be sealed and pressurized to transfer the sample fluid (30) within the sample source (4) through the inlet element (29) into the inlet region (23) of a flow channel (3)(see for example, FIG. 2B which provides a seal element (43) configured to engage a welled plate (32) to seal each of the plurality of wells (44)). In particular embodiments of the invention, the plurality of sample sources (4), such as the welled plate (32) can be located in a pressure regulated vessel (45) allowing adjustment of pressure (46) within the pressure regulated vessel (45) as necessary or desired to transfer the sample fluid (30) (whether or not containing a plurality of particles (22)) from each of the plurality of sample sources (4) to the corresponding plurality of flow channels (3) of the microfluidic chip (2).

Again referring primarily to FIGS. 2A and 2B, in the alternative, each of the plurality of inlet elements (29) can be coupled to a pump (47), such as peristaltic pumps (coupled to the flexible external surface (42) of each of the plurality of inlet elements (29) or syringe pumps (the sample source (4) being the barrel of the syringe pump) fluidicly coupled to the inlet region (23) to generate a flow of sample fluid (30) within each of the plurality of inlet elements (29) to the inlet region (23) of each of the corresponding plurality of flow channels (3).

Again referring primarily to FIGS. 2A and 2B, in the alternative, the collection region (28) of each of the plurality of flow channels (3) can be fluidically coupled to a pump (47) such as a peristaltic pump, a vacuum pump, or the like which operates to draw or aspirate an amount of sample fluid (30) through the corresponding inlet element (29) into the inlet region (23) of the corresponding flow channel (3) and subsequently to the collection region (28) of the flow channel (3).

The flow rate (48) of each of the one or more sample fluid streams (21) in the corresponding one or more flow channels (3) can, depending on the embodiment, be adjusted by either increasing or decreasing the pressure (46) within one, a portion, or all of the plurality of sample sources (4) within a range of 3 pounds per square inch ("psi") and about 50 psi, or in a range of about 5 psi and about 15 psi, or in a range of about 10 psi and about 11 psi, or alternately by, increasing or decreasing the amount of sample fluid (30) pumped or drawn into each flow channel (3) by the pumps (47). By adjusting the flow rate (48) of the sample fluid stream (30) within each of the plurality of flow channels (3), the particle velocity (49) of the plurality of particles (22) can be correspondingly adjusted within the plurality of flow channels (3) within the range of about 0.1 meters per second and about 20 meters per second, or at any particular particle velocity within the range in increments of about 0.1 meters per second. A particle velocity (49) of between about one and three meters per second can be achieved in each of the plurality of flow channels (3). However, between the plurality of flow channels (3) the particle velocity (49) can be substantially similar or can be substantially dissimilar. As one non-limiting example, referring to FIG. 17, the particle velocity (49) of certain of the plurality of flow channels (3) can be substantially lower (channel 9) and the particle velocity (0 of certain of the plurality of flow channels (3) can be substantially higher (channels 15 and 20) without substantially effecting the analysis or separation of the particles (22), as further described below.

Now referring primarily to FIG. 5A, regardless of the inlet element pattern (31) of the plurality of inlet elements (29) each inlet element (29) can have a configuration which allows the sample fluid (30) within each of the plurality of sample sources (4) along with the entrained plurality of particles (22) to be delivered to the inlet region (23) of the corresponding plurality of flow channels (3). The plurality of sample fluid streams (21) generated in the inlet region (23) of each of the plurality of flow channels (3) can flow from the inlet region (23) into the primary focusing region (24) of each of the plurality of flow channels (3).

The primary focusing region (24) of the channel (3) can be configured to deliver the plurality of particles (22)(or at least one or a suitable number of particles (22)) to the detection region (26) of each of the plurality of flow channels (3) generally centered (or referred to as "centration") (51) in the sample fluid stream (21) and having sufficient inter-particle spacing (50) to allow individual serial interrogation of the plurality of particles (22) in the fluid stream (21). The particle velocity (49) can be adjusted to allow a suitable number of the plurality of particles (22) to pass through the detection region (26) for interrogation each second, although there will be a certain portion of the plurality of particles (22) too closely associated within the detection region (26) to individually interrogate regardless of the degree of centration (51) or particle velocity (49) within the flow channel (3).

As to particular non-limiting embodiments, the primary focusing region (24) can of a flow channel (3) can have similar cross-sectional dimension to the inlet region (23) or the detection region (26), or both. As to these embodiments, the inter-particle spacing (50) within the sample fluid stream (30) in each flow channel (3) can be adjusted by adjusting the concentration of the plurality of particles (22) in the sample fluid (30) within the sample source (4). The lesser the concentration of the plurality of particles (22) in the sample fluid (30), the greater the inter-particle spacing (50) can be in the sample fluid stream (21) in each flow channel (3). Accordingly, as to these embodiments, the inlet region (23) and the primary focusing region (24) can have a combined length sufficient to allow the plurality of particles (22) in the sample fluid stream (21) to achieve sufficient centration (51), inter-particle spacing (50), and particle velocity (49) in relation to the particular configuration of the flow channel (3) for serial interrogation of the plurality of particles (22) in the detection region (26). For example, where the primary focusing region (24) has a cross-sectional configuration similar to the inlet region (23) and the detection region (26) of the flow channel (3), the primary focusing region (23) can have a length in the range of 100 µm and 500 µm. A substantial advantage of embodiments in which the configuration of the primary focusing region (23) has a cross-sectional configuration similar to the configuration of the detection region (26) can be that the plurality of channels (3) disposed in the microfluidic chip (2) can be substantially less complex than other embodiments of the plurality of flow channels (3), as further described below, and can be very substantially less complex than conventional flow cytometers with regard to the configuration and number of components to promote conventional laminar flow of a sample fluid stream (30) within a sheath fluid stream (52). The particular embodiment above-described can entirely eliminate the need for and the use of a sheath fluid stream (52) and the use of components to promote laminar flow. Instead, the plurality of particles (22) can be entrained at a suitable concentration in the each of the plurality of sample sources (4) and introduced into the primary focusing region (24) of the corresponding plurality of flow channels (3), without or avoiding the use of a sheath fluid stream (52) and without use of laminar flow as conventionally defined in the field of flow cytometry in which a sheath fluid stream (52) surrounds the sample fluid stream (21). Moreover, the plurality of particles (22) in each of the plurality of flow channels (3) can have similar or even greater event rates, sort rates and purity rates as can be obtained by use of conventional flow cytometers and conventional laminar flow cytometry methods. Accordingly, as to certain embodiments of the invention, and referring now primarily to FIG. 5, the sheath fluid streams (53)(54), the two sheath fluid channels (55)(56), sheath fluid channel inlets (57)(58), and the secondary sheath fluid channels (59)(60) can in part or in whole be omitted.

Now referring primarily to FIG. 5A, certain non-limiting embodiments of the invention can include a primary focusing region (24) of each of the plurality of flow channels (3) configured to provide two channel side walls (61)(62) which angle inwardly approaching the detection region (26) of each of the plurality of flow channels (3). This configuration of the primary focusing region (24) can operate to increase centration (51) of the plurality of particles (22) within the sample fluid stream (21) and gradually increase the particle velocity (49) within each of the plurality of flow channels (3) as the plurality of particles (22) approach the detection region (26) of each of the plurality of flow channels (3).

As to each of the plurality of flow channels (3), two sheath fluid channels (55)(56) can be connected upstream from the location at which the sample fluid stream (21) entraining the plurality of particles (22) joins the primary focusing region (24) of the each flow channel (3). Each of the two sheath fluid channels (55)(56) can have a separate sheath fluid channel inlet (57)(58) which allows introduction of a corresponding two sheath fluid streams (53)(54) at opposed sides (63)(64) of the wide end (65) of the primary focusing region (24). The two sheath fluid streams (53)(54) can converge approaching the detection region (26) of each of the plurality of flow channels (3). The sample fluid stream (21) entraining a plurality of particles (22) can join the converging flow of the two sheath fluid streams (53)(54) without substantial mixing to generate a sample fluid stream (21) generally surrounded by a sheath fluid stream (52) entering the detection region (26) of each of the plurality of flow channels (3).

Again referring primarily to FIG. 5, as to certain embodiments a secondary focusing region (25) can further provide two secondary sheath fluid channels (66)(67) can intersect the flow channel (3) down stream of the primary focusing region outlet (68) and upstream of the detection region (26). Each of the two secondary sheath fluid channels (66)(67) can introduce a corresponding two secondary sheath fluid streams (68)(69) into a secondary focusing region (25) of each of the plurality of flow channels (3). Introduction of the two secondary sheath fluid streams (68)(69) can act to further narrow and center the cross-sectional area of the sample fluid stream (21) in each of the plurality of flow channels (3) as it enters the detection region (26).

The two secondary sheath fluid channels (66)(67) each extend from a secondary sheath fluid channel inlet (70)(71) disposed substantially parallel to the sheath fluid channels (55)(56) and then extend substantially transverse or perpendicular to connect with the secondary focusing region (25) of each of the plurality of flow channels (3). Connection of the secondary sheath fluid channel outlets (72)(73) above and substantially parallel to sample fluid stream (21) in the secondary focusing region (25) can result in a sample fluid stream (21) entering the detection region (26) of the plurality of flow channels (3) focused inwardly away from each of the side walls (74) of each of the plurality of channels (3). The sample fluid stream (21), as to particular embodiments of the invention, can be purposefully focused off center by use of the various configurations above-described.

Now referring primarily to FIGS. 1, 2A, 3A, and 4A, a plurality of detection regions (26) of a corresponding plurality of flow channels (3) can be disposed in the microfluidic chip (2) in substantially parallel relation spaced a distance apart in the range of about 700 μm and about 3500 μm depending upon the embodiment and the application. As shown in FIGS. 2A and 3A, the spacing between a plurality of flow channels (3) in the detection region (26) can bring the plurality of channels (3) in closer relation than as shown in FIGS. 4A and 5A. Arranging the plurality of channels (3) in closer relation within the detection region can provide an advantage with respect to particular embodiments of the optical detection system (74), as further described below.

Figure 6:
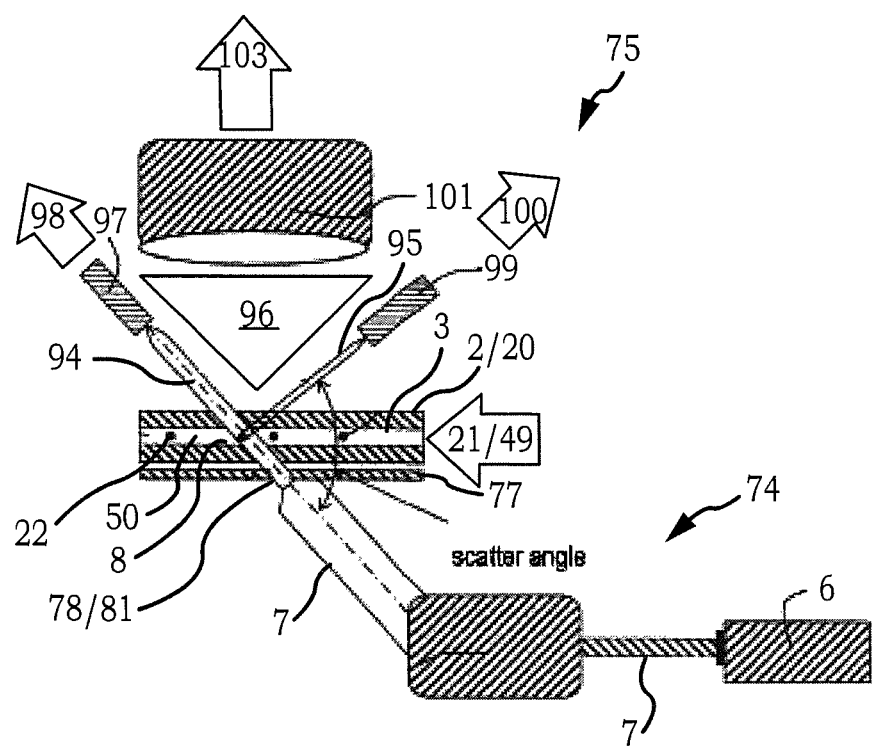
FIG. 6 is a schematic diagram of a particular embodiment of an optical detection system of the present invention.
Figure 7:
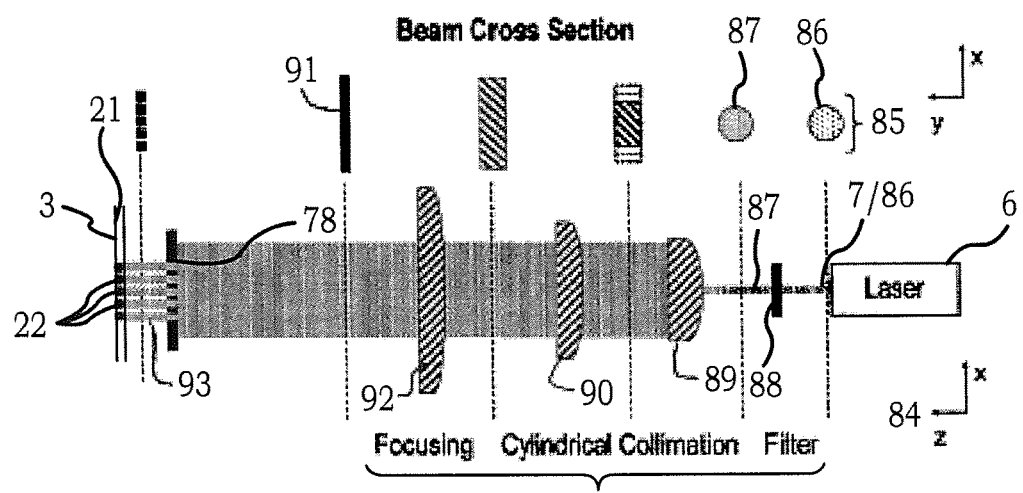
FIG. 7 is a schematic of a particular embodiment of a beam shaping optics suitable for use in the embodiment of the optical detection system of FIG. 6.

Now referring primarily to FIGS. 6 and 7, embodiments of the microfluidic multiple flow channel particle analysis system (1) can further include an optical detection system (74) which in part includes a light source (6) adapted to locate a beam of light (7) incident upon an optical window (8) of each of said plurality of flow channels (3) within the detection region (26) of each of the plurality of flow channels (3). The light source (6) can include one or more laser(s) each of which emit a beam of light (7) (whether continuous or pulsed) which engages beam shaping optics (75) to direct one or beams of light (7) incident upon the optical window (8) of each of the plurality of flow channels (3). As one non-limiting example, the beam of light (7) can be split into one or more beams of light (7) each incident upon the optical window (8) of each one of the plurality of flow channels (3). A portion of the beam of light (7) can be admitted into the optical window (8) of the corresponding one of the plurality of flow channels (3). As to particular embodiments, the optical window (8) as to each of the plurality of flow channels (3) can be configured to have a substantially lesser width than the width of the corresponding one of the plurality of flow channels (3). The lesser width of the optical window (8) can admit the beam of light (7) proximate the center of each of the plurality of flow channels (3) to establish an optical core (76) within each of the plurality of flow channels (3) and thereby within each corresponding one of the plurality of fluid streams (21). By generating the optical core (76) within each of the plurality of flow channels (3), the beam of light (7) interrogates that portion of the plurality of particles (22) which are sufficiently centered (51)(or have sufficient centration) in each of the plurality of fluid streams (21) to pass within the optical window (8) of lesser width (those particles within the optical core (8)) and does not interrogate that portion of the plurality of particles (21) which flow outside of the lesser width optical window (8). Interrogating only that portion of the plurality of cells (21) in the optical core (76) results in essence or effect centration (51) of the plurality of particles (22) for analysis and separation events, more thoroughly described below.

Using the illustrative non-limiting example of a plurality of beams of light (7), the optical window (8) (whether of greater or lesser width within each of the plurality of flow channels (3)) can be created by directing each one of the plurality of beams of light (7) toward an optical mask (77) which aligns a first aperture element (78), and as to certain embodiments a second aperture element (79)(as shown in FIGS. 5 and 11), in relation to the detection region (26) of each of the plurality of flow channels (3) disposed in the microfluidic chip (2). The beam of light (7) admitted through the first aperture element (78) and the second aperture element (79)(or more apertures as to certain embodiments) of the optical mask (77)) can have a waist focused on or before or after the plane in a corresponding first optical window (8) and second optical window (80) through which the plurality of particles (22) entrained in the corresponding plurality of fluid streams (21) pass. Thereby, each of the plurality of particles (22) can be interrogated by a beam of light (7) twice passing through the detection region (26), once as it passes through the first optical window (8) and a second time as it passes through the second optical window (80).

As to certain embodiments of the invention, the first aperture element (78) can provide a generally rectangular first aperture opening (81) having width of about 40 μm and a length centrally aligned with the longitudinal axis (82) of the detection region (26) of the flow channel (3) of about 20 μm (although useful configurations can provide a width up to about 60 μm and length of up to about 60 μm in various permutations and combinations depending upon the application). The second aperture element (79) can define a generally rectangular second aperture opening (83) having width of about 40 μm and a length centrally aligned with the longitudinal axis (82) of the detection region 26) of about 40 μm (although useful configurations can provide a width up to about 60 μm and length of up to about 60 μm in various permutations and combinations depending upon the application). The distance between the trailing edge of the first aperture opening (81) and the leading edge of the second aperture opening (83) can be in the range of about 10 μm and about 50 μm. The time of passage of a particle (22) in relation to the first aperture opening (81) and the time of passage of the particle (22) in relation to the second aperture opening (83) can be determined and utilized to determine the particle velocity (49) of each the plurality of particles (22) interrogated within the detection region (26) of each of the plurality of flow channels (3).

As to certain embodiments, a suitable light source (6) can be a 532 nm 10 W laser (Millenia Prime 532 CW DPSS laser) available from Newport Spectra Physics, or a 532 nm 6-7 W laser (Finesse 7 W Laser) available from Laser Quantum, or Verdi G7 532 nm 7 W laser from Coherent Laser. Also suitable for use with embodiments of the invention is a 488 nm 2 W or greater coherent laser (Genesis Blue series models available from Coherent Laser). As to other embodiments, an optically pumped solid state ("OPSS") laser can be used, capable of generating various different excitation wavelengths to perform interrogation of the plurality of particles (22) within the detection region (26) of each of the plurality of flow channels (3). Alternately, a pulsed laser such as a Vanguard 350-HDM, Newport Spectra-Physics or a Genesis CX355-250 from Coherent Laser can be used to produce a pulsed beam of light (50). However, these specific examples are not intended to be limiting.

Now referring primarily to FIG. 7, a cross-section of a non-limiting embodiment of beam shaping optics (75) suitable for use in embodiments of the optical detection system (74) of the invention is drawn in the x-z plane with the overall direction of light propagation (84) along the z axis. Each broken line leads up to a light beam x-y profile sketch (85) to show how the beam of light (7) can be manipulated by the beam shaping optics (75). The light beam (7) can pass from a single laser output (86) of nearly round profile of about 700 microns in diameter to a wavelength filtered beam (87) after a low pass or band pass filter (88). The light beam (7) then passes through a first pair of cylindrical collimation lenses (89)(90) having focal length of about 5 mm and a focal length 250 mm respectively, to produce a substantially rectangular-shaped light beam (91). The light beam (7) then passes through a focusing lens (92) having focal length of about 150 mm to produces a sharpened the light beam (7) of about 100 microns in the y-axis. The overall profile can be 36 mm by 100 micron which can be used to illuminate the detection region (26) of a plurality of flow channels (3) of the microfluidic chip (2) admitted by the first aperture element (78) and the second aperture element (79) in the optical mask (77). A light beam (7) of this particular profile can be made incident upon seventy two flow channels (3) spaced a distance apart of about 900 microns, or an even greater plurality spaced closer together. In a microfluidic chip (2) having the N apertures in the optical mask (77) spaced on about 900 micron centers the beam can be adjusted to be slightly more or less than N×900 microns along the x-axis and about N×900 microns along the y-axis. The collimated and shaped light beam (7) can be made incident upon the first aperture opening (81) and the second aperture opening (83) of the optical mask (77) and can become N aperture element shaped light beams (93) each with a waist focused within the first optical window (8) and the second optical window (80) of each of a plurality of flow paths (3). In the illustrative embodiments of FIGS. 2A and 3A, the distance across the plurality of flow channels (3) encompassed by the detection region (26) can be about 10 millimeter ("mm") wide and about 4 mm long (along the detection region (26) of each of the plurality of channels (3)); however, the invention is not so limited.

Particular embodiments of the optical detection system (74) can provide a reflective beam splitter which includes a segmented mirror for splitting an incident light beam into a plurality of light beams. The collimated incident light beam enters the reflective beam splitter and can be reflected off an incidence mirror which can be used to set the correct angle of incidence (generally a low angle) for collimated light beam on the segmented mirror. The resulting plurality of light beams can extend upwards (or downwards or other direction depending on the orientation of microfluidic and optical components) substantially parallel or as directed by the segmented mirror to the incident beam as described by U.S. Pat. No. 7,492,522, hereby incorporated by reference herein.

Again referring primarily to FIG. 6, certain properties of the light beam (7) can be measured in relation to each of the plurality of particles (22) such as light extinction (94)(also referred to as "optical extinction"), angle dependent side scatter (95) and emitted light (96). Light extinction (94) refers to that fraction of the light beam (7) that passes through each of the plurality of channels (3) without interaction with each of the corresponding plurality of particles (22). Angle dependent side scatter (95) refers to the fraction of the light beam (7) that is scattered or bent at each angle (theta) away from the light beam (7) incident on each of the plurality of particles (22). Emitted light (96) (which can be an amount of "fluorescent light") refers to the fraction of the light beam (7) absorbed by substances bound or associated with each of the plurality of particle (22) and emitted at a longer wavelength.

Figure 10:
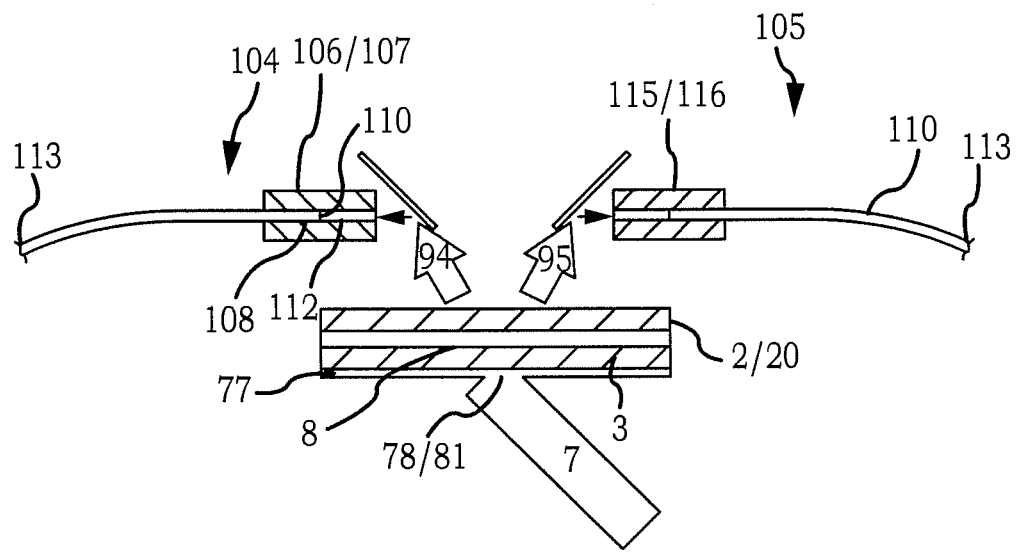
FIG. 10 is a cross-sectional view of a particular embodiment of an optical detection system for the detection of light extinction and side scatter in a plurality of flow channels of multiple flow channel microfluidic chips such as those shown in FIGS. 2A, 3A, 4A and 5A.

An optical extinction detector (97) can be placed directly opposite and in line with the axis of the light beam (7) admitted through the first aperture opening (81) and the second aperture opening (83) in the optical mask (77) to receive that fraction of the light beam (7) not incident on each of the plurality of particles (22) interrogated (the "optical extinction") (or the light extinction (94) can be directed by optics to the optical extinction detector (97) as shown for example in FIG. 10). An optical extinction detector (97) optically coupled to each of the plurality of flow channels (3) can produce a light extinction signal (98) which varies based on the portion of the beam of light (7) which passes through the first optical window (8) and the second optical window (80) of the corresponding one of the plurality of flow channels (3).

An optical scatter detector (99) can be placed substantially perpendicular to the axis of the light beam (7) admitted through the first aperture opening (81) and the second aperture opening (83) in the optical mask (77) to receive that fraction of the light beam (7) scattered perpendicular to the axis of the light beam (7) (or the angle dependent scatter can be directed by optics to the optical scatter detector (99)). Optical scatter detectors (99) for other angles may optionally be placed at those angles in that same plane. An optical scatter detector (99) optically coupled to each of the plurality of flow channels (3) can produce a light scatter signal (100) which varies based on the portion of the beam of light scattered from the optical window(s) (8)(80) of the corresponding one of the plurality of flow channels (3).

An emitted light detector (101)(see for example FIGS. 1 and 13) can receive emitted light (96) generated by the substances associated or bound to each of the plurality of particles (22). A high numerical aperture lens (102) can located between the detection region (26) of each the plurality of flow channels (3) and the emitted light detector (101) to accept emitted light (96) over a range of angles and image the emitted light (96) on the emitted light detector (101). An emitted light detector (101) optically coupled to each of the plurality of flow channels (3) can produce a light emission signal (103) which varies based on the amount of emitted light (96) passing from the optical window(s) (8) (80) of the corresponding one of the plurality of flow channels (3).

The light source (6) along with beam shaping optics (75) as shown in FIG. 7 can make the light beam (7) or each of the plurality of light beams (7) incident upon the detection region (26) of each flow channel (3) at about a 45-degree angle. In this manner, the light extinction (94) extends in the same direction on the opposite side of the detection region (26) of the flow channel (3). The angle dependent side scatter (95) can extend at a 45-degree angle from the detection region (26) of each of the plurality of flow channels (3)(substantially perpendicular to the optical extinction). This provides a cone of optical freedom having a more or less 90 degree unobstructed path for the emitted light (96) in between the light extinction (94) and angle dependent side scatter (95).

Figure 8:
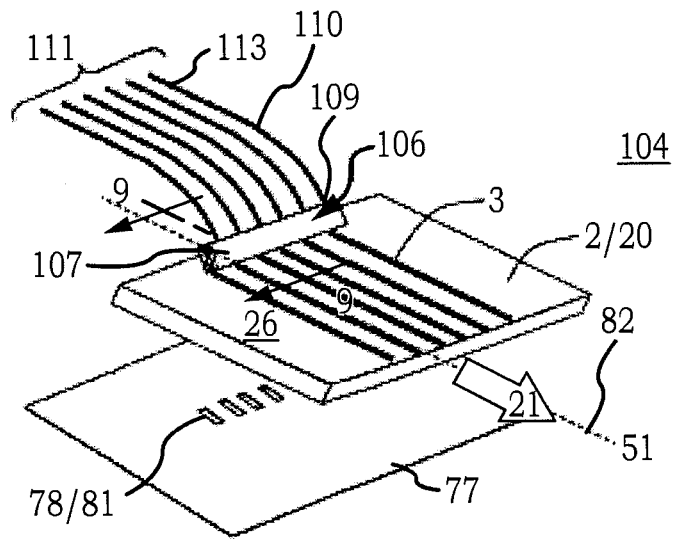
FIG. 8 is a schematic diagram of a particular embodiment of an optical detection system for detecting light extinction concurrently in a plurality of flow channels of multiple flow channel microfluidic chips such as those shown in FIGS. 2A, 3A, 4A and 5A.
Figure 9:
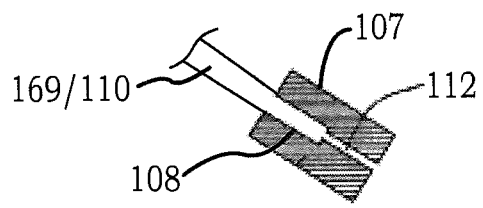
FIG. 9 is a cross-sectional view 9-9 of a portion of the light path within the subsystem for detecting light extinction shown in FIG. 8.

Now referring primarily to FIGS. 8 through 10 which show a particular non-limiting embodiment of an optical extinction detection system (104) and an optical scatter detection system (105). Now referring primarily to FIGS. 8 and 9, as a non-limiting example, the optical extinction detection system (104) can include an optical extinction collimated ribbon detector (106) located above the detection region (26) of a microfluidic chip (2) having a plurality of detection regions (26) with inter-channel spacing of about 900 microns. The optical extinction collimated ribbon detector (106), a cross-section of which is shown in FIG. 9, can include a single piece ribbon connector (107) having a plurality of holes (108) each of about 300 micron diameter and a depth of less than the ribbon thickness, and spaced about 900 microns on centers so as to align with the aperture openings (81)(83) of the optical mask (77). The first end (109) of a high numerical aperture fiber (110) can be engaged within each hole (108) to form an array of fibers (111) with one fiber (110) for each of the plurality of detection regions (26) of the plurality of flow channels (3). A collimating hole (112) of smaller diameter but concentric with a hole (108) communicates between each hole (108) and the surface of the ribbon connector (107). This collimating hole (112) receives the light extinction (94) of the light beam (7) passed through the corresponding aperture openings (81)(83) of the optical mask (77) and centers the light extinction (94) onto the optical fiber (110) engaged with the corresponding one of the plurality of holes (108) in the ribbon connector (107). The light extinction collimated detector ribbon (106) can have each collimating hole (112) aligned with a corresponding aperture openings (81)(83) of the optical mask (77) at an angle aligned to receive the light extinction (94) of the light beam (7) (for example at an angle of 180 degrees) passing through microfluidic chip (2). The collimating hole (112) can have cross-sectional area in excess of area of the aperture openings (81)(83) in the optical mask (77) to allow substantially all of the light extinction (94) that crosses the aperture openings (81)(83) in the optical mask (77) to be received by the optical fiber (110) at the end of the collimating hole (112). The collimating hole (112) can be of sufficient length to reject any stray light passing through the aperture openings (81)(83) in the optical mask (77) corresponding to the detection region (26) of other of the plurality of flow channels (3). As a non-limiting example, the aperture (81)(83) in the optical mask (77) can be about 50 μm×50 μm square, the collimating hole (112) can be about 150 μm diameter, the optical fiber (110) can be about 300 μm diameter, and the surface of the ribbon connector which communicates with the collimating hole (112) can be located within about 2 mm of the of the surface of the microfluidic chip (2), or can be located a further distance with directional optics (such as a mirror). The second end (113) of each optical fiber (110) can be optically coupled to an optical extinction detector (97) or other optical detector. Light extinction (94) may be sufficiently bright to use a photodiode (114) as the light extinction detector (97).

Now referring primarily to FIG. 10, the optical scatter detection system (105) can include a side scatter collimated ribbon detector (115) constructed substantially the same as the optical extinction collimated ribbon detector (106) above described but positioned at an angle to the optical extinction (94) (for example, 90 degrees). One skilled in the art will recognize that similar ribbon detectors can be positioned at other angles to observe other scattering parameters. The forward scatter which comprises optical scattering in the forward direction generally in close proximity to the optical extinction (94) can be collected by positioning (nearly at 180 degrees from incident) a second ribbon connector (116) as close to the light extinction (94) as possible without acquiring the light extinction (94). The second end (113) of the optical fiber (110) can be optically coupled to an optical scatter detector (99) which can be a photomultiplier tube or photodiode, as above described.

Now referring primarily to FIG. 11, which provides a non-limiting example of emitted light optics (117) for emitted light (96) detection. The emitted light optics (117) can include a first lens (118). The first lens (118) can be a high numerical aperture (low F#) lens configured and located in relation to the detection region (26) of the plurality of flow channels (3) to increase capture of emitted light (96) from each of the plurality of particles (22) interrogated. A non-limiting example of a suitable lens is a Leica Noctilux 50 mm F#1 lens. A spectral blocking element (119) can be located above the first lens (118). The spectral blocking element (119) acts to filter out certain wavelength(s) of the emitted light (96). As a non-limiting example of a suitable spectral blocking element (96) can be a 520LP or a 545LP filter available from Chroma Technology Corp. A second lens (120) can be positioned to deliver the emitted light (96) of each of the plurality of particles (22) to an image plane (121). An optical fiber array (122) extends from the image plane (121) to a corresponding array of a plurality of emitted light detectors (101). Each optical fiber (123) of the fiber array (122) can be capable of conveying a portion of the emitted light (96) from the image plane (121) to a corresponding one of the plurality of emitted light detectors (101). Each of the plurality of emitted light detectors (101) can be a photomultiplier tube capable of receiving a range of wavelengths of the emitted light (96) from the image plane (121). A focusing lens (124) can be located between each optical fiber (123) and each emitted light detector (101).

Figure 12:
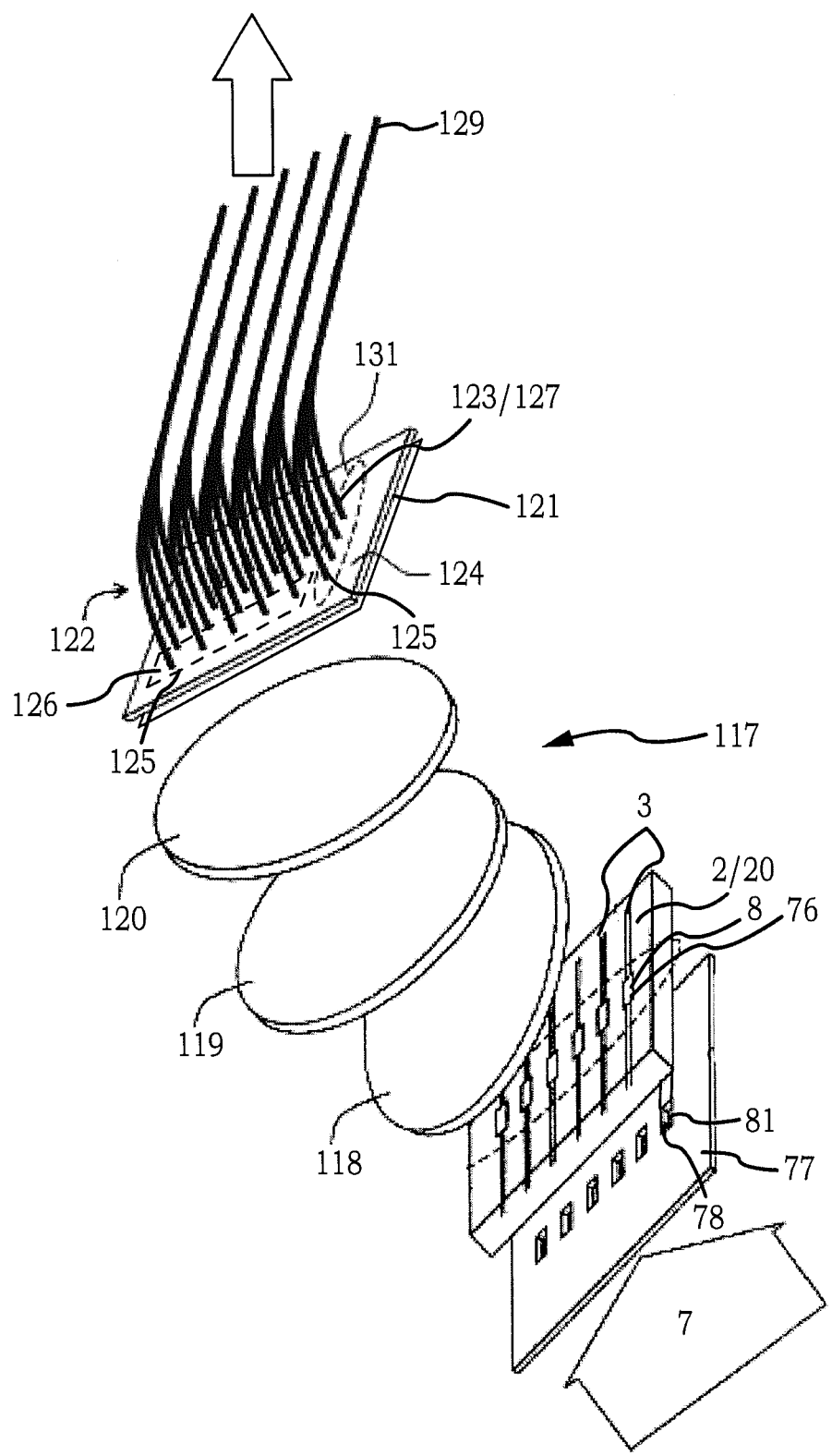
FIG. 12 is a perspective view of a particular embodiment of an optical detection system for the detection of light extinction, side scatter and emitted light in a plurality of flow channels of multiple flow channel microfluidic chips such as those shown in FIGS. 2A, 3A, 4A and 5A.

Now referring primarily to FIG. 12, an opaque plate (124) can provide bores (125) (for example the linear row of bores (126) each having a diameter of about 400 um) which communicate between opposed sides of the opaque plate (124) can each correspondingly engage an optical fiber (123) (for example an optical fiber (123) having a diameter of about 400 um). The bores (125) can be located in the opaque plate (124) to correspondingly locate the first end (127) of each optical fiber (123) in relation to the image plane (121) to capture a portion of the bandwidth of the emission spectra or peak emission from each of the fluorophores (128): FITC, PE, APC and PerCP. Each optical fiber (123) can capture an emission bandwidth of about 10 nm. A corresponding emitted light detector (101) (for example, single anode H6780-20 or 32-anode H7260-20, or 64-anode R5900 or H7546B-20 series photomultiplier tubes available from Hamamatsu, Inc. or other similar multiple or single anode photomultiplier tubes) can be made responsive or optically coupled to the emission spectra conveyed to the second end (129) of an optical fiber (123). As a non-limiting example, the second end (129) of each optical fiber (123) can be coupled to the photocathode window of a photomultiplier tube at a location corresponding to a single anode, to amplify the emission spectra and generate a emitted light signal (103) which varies in relation to the amplitude of the emission wavelength transmitted to the second end (129) of an optical fiber (123). Other light amplifying detectors such as image intensifiers or avalanche photodiode arrays or others known to those skilled in the art of optics may also be used to detect the emission spectra and convert them to an emitted light signal.

The emitted light optics (117) above described can be used in those embodiments of the microfluidic chip (2) having a plurality of flow channels (3) each having a detection region (26). The optical mask (77) can block a substantial portion of the incident light and narrow the beam of light to a sufficiently small area of each detection region (26) of each of the plurality of channels (3) to isolate the emitted light (96) to a correspondingly small area of the optical detection optics (117), above described. The optical column of the first lens (118), spectral blocking element (119) and second lens (120) can be of sufficient dimension to provide a field of view in excess of the detection region (26) of the microfluidic chip (2). The emitted light (96) from the detection region (26) of each of the plurality of channels (3) of the microfluidic chip (2) can be sufficiently isolated from one another on the image plane (121) for individual analysis. The opaque plate (124) can for example, locate a linear row of optical fibers (126) in relation to the image plane (121) to receive the emitted light (96) from each detection region (26) of a plurality of channels (3); and while the example of FIG. 12 shows six optical fibers (123) corresponding to the emitted light (96) from each of six detection regions (26) of six flow channels (3), the invention is not so limited, and greater or lesser number of optical fibers (123) can be located in a linear row to receive the emitted light (96) from interrogation of a plurality of particles (22) in a plurality of flow channels (3), such as 2, 4, 16, 24, 48, 96, 254, and so forth.

The above described or similar or equivalent emitted light optics (117), can be used for analysis of each of the plurality of particles (22) bound to antibodies (130) labeled with fluorophores (128) or other fluorescent particle markers known to those skilled in the art of cytometry. As non-limiting examples, the plurality of particles (22) can be bound to antibodies (130) labeled with the fluorophores (128) such as fluorescein isothiocyanate ("FITC"), R-Phycoerythrin ("PE"), AlloPhycoCyanin ("APC") and Peridinin-chlorophyll-protein Complex ("PerCP") which have peak fluorescence emission at 518 nm, 575 nm, 660 nm, and 675 nm respectively. The emission spectra from FITC, PE, APC and PerCP can be separated by the optics at the image plane (121). In regard to particular embodiments, more than one light beam (7) (such a more than one laser beam) can be made incident upon the plurality of particles (22) to interact with and or excite additional fluorophores or other properties of the particles.

The range of the emission spectrum of the emitted light (96) can be further divided into a plurality of narrower emission ranges (131) for amplification and analysis. As to certain embodiments as shown in FIG. 12, the emission range (131) of the emitted light (96) corresponding to each threshold event (14) in each flow channel (3) of the microfluidic chip (2) can for example be divided into four narrower emission ranges. The emitted light (96) of each emission range can be conveyed to a corresponding emitted light detector (101) (for example, single anode H6780-20 or 32-anode H7260-20 or 64-anode R5900 series photomultiplier tubes from Hamamatsu, Inc.).

Now referring primarily to FIG. 5, the ingress and egress of each of the plurality of particles (22) in relation to the first aperture opening (81) and the second aperture opening (83) affords four event thresholds which can have gated criteria (13) with respect to the light extinction signal (98). Each of the plurality of particles (22) which satisfactorily achieves the gate criteria (13) for all four event thresholds with respect to light extinction signal (98) results in a "threshold event" (14) for further analysis, gating, and timing calculations for down stream sorting events, further described below. Each of the plurality of particles (22) detected by only one to three event thresholds may still be counted, but can be rejected since reliable analysis and variable measurement may be achievable only as to a threshold event (14).

The multiple flow channel particle analysis structure (1) can further include an analyzer (11) having multiple first in first out levels which operates to continuously concurrently analyze for threshold events (14) within each of said plurality of flow channels (3). Now referring to FIG. 16, as a non-limiting example, the analyzer (11) can concurrently assess threshold events (14) in each one of twenty four flow channels (3). The concurrent analysis of all twenty four flow channels (3) for threshold events can occur even though there may be a substantial difference between the threshold event rate (132) for certain of the plurality of flow channels (3) (for example flow channels 15 and 19 have substantially different threshold event rates).

The term "concurrently" for the purposes of this invention means the capability of simultaneous uninterrupted interrogation and analysis of a plurality of flow channels without restriction as to any one or more of the plurality of flow channels in regard to the flow of the fluid stream, entrainment of particles in the fluid stream, incidence of the light beam, detection, signal generation, or electronic processing.

Examples of the term "restriction" include one or more of serial intermittent illumination of a plurality of flow channels, scanned illumination of a plurality of flow channels, pause in the flow of the fluid stream in one or more of the plurality of flow channels, pause in entrainment of particles from one or more sample sources, detection of one or more of light extinction, side scatter, or emitted light of one or more flow channels in a non-parallel fashion, non-parallel signal generation, or non-parallel data acquisition or processing.

The analyzer (11) can transform each of threshold events (14) into threshold event data unit (16) which allows each one the threshold events (14) in each of the plurality of channels (3) to be individually and independently triggered and gated which allows for simultaneous processing of different sample fluids (30) entraining different particles (22) in each one of a plurality flow channels (3). For example, the sample fluid (30) or the plurality particles (22) in a first sample source (4) can each be different than the sample fluid (30) or the plurality of particles (22) in a second sample source (4) with respect to a large number of factors such as: particle type, particle size, concentration of particles per milliliter, the viscosity of the sample fluid, the velocity of the particles in a particular one of the plurality of samples, optical extinction characteristics, optical scatter characteristics, optical emission characteristics, number of subpopulations, or the like.

The analyzer (11) can operate to assess threshold events (14) at a rate of between zero threshold events (14) and about 100,000 threshold events (14) per second occurring in each one of the flow channels (3). As to certain embodiments, the analyzer (11) can operate to assess threshold events (14) at rate selected from the group consisting of between about 1000 and about 5000, between about 2,500 and about 7,500, between about 5,000 and about 10,000, between about 7,500 and about 12,500, between about 10,000 and about 20,000, between about 15,000 and about 25,000, between about 20,000 and about 30,000, between about 25,000 and about 35,000, between about 30,000 and about 40,000, between about 35,000 and about 45,000, between about 40,000 and about 50,000, between about 45,000 and about 55,000, between about 50,000 and about 60,000, between about 55,000 and about 65,000, between about 60,000 and about 70,000, between about 65,000 and about 75,000, between about 70,000 and about 80,000, between about 75,000 and about 85,000, between about 80,000 and about 90,000, between about 85,000 and about 95,000, between about 90,000 and about 100,000, or even a greater number of threshold events, and combinations thereof between said plurality of flow channels.

As an illustrative non-limiting example, a microfluidic chip (2) having ten flow channels (3) with threshold events (14) occurring at a rate of 100,000 threshold events per second in each of the ten flow channels (3) can have a combined rate of 1,000,000 threshold events per second over the ten flow channels (3).

Now referring primarily to FIG. 1, as to certain embodiments of the invention, the light scatter signal (100) or the emitted light signal (103) (whether analog or digital) generated respectively by each of the scattered light detector (101) or the emitted light detector (101) can be received by a corresponding signal integrator (133). The light scatter signal (100) and the emitted light signal (103) for each threshold event (14) occurring in each of the plurality of channels (3) can be integrated over period within a range of about 10 us to about 100 us. As to certain embodiments of the invention, an analog signal (134) from a plurality of flow channels (3) can be converted directly to digital format, and the signal integration can be done over a converted digital signal (135) inside a Field Programmable Gate Array (136). As one non-limiting example, described below for the analysis of anti-CD-3-PE labeled cells an analog signal (134) for each threshold event (14) was integrated over 80 us. The digital signal (137) from a plurality of flow channels (3) can be further analyzed and the noise from common-mode sources and cross-talk removed.

The integrated values (138) from the plurality of signal integrators (133) can be received by a multiplexer (132) such that the integrated values (138) of the threshold events (14) from each of a plurality of flow channels (3) can share common data collection and data analysis sharing a single multiplexer output signal (139) which carries as many output communication signals (140) as necessary to maintain the desired sustained combined threshold events (14) of a desired plurality of flow channels (3). The multiplexer output signal (139) can be converted to a digital signal (137) which can be processed by one or more processing units (141) that may reside inside a Field Programmable Gate Array (136), in relation to an executable particle analysis processing steps (15) and executable particle separation processing steps (17) which function to convert the digital signal (137) into timed events (18) for separation (also referred to as sorting) of the plurality of particles (22) within each of the plurality of flow channels (3) based on threshold event criteria, gating parameters of light extinction (94), scattered light (95), and emitted light (96) as further described below, and into graphic data (142) by operation of a graphic data generator (such as shown in FIGS. 19A-19F as further described below).

As for particular embodiments of the invention, threshold event data units (16) from different flow channels (3) can be analyzed in real-time or post-processed to provide a set of normalization values permitting common or grouped gating settings. Once this set is generated, normalization may be applied in real-time to each threshold event data unit (16).

As for certain embodiments of the invention, threshold event data units (16) from different flow channels (3) may be analyzed in real-time or post-processed to provide a set of compensation values allowing better differentiation between particles. Once this set is generated, compensation may be applied in real-time to each threshold event data unit.

As for certain embodiments of the invention, the plurality of channels (3) may be divided in smaller pluralities of flow channels (3), each using different sets of normalization, compensation and gating parameters, allowing different types of sorting within the same run.

As for certain embodiments of the invention, the digital signal (137) from a plurality of flow channels (3) may be combined to augment the amount of information available that each flow channel (3) may use for gating purposes.

Figure 13:
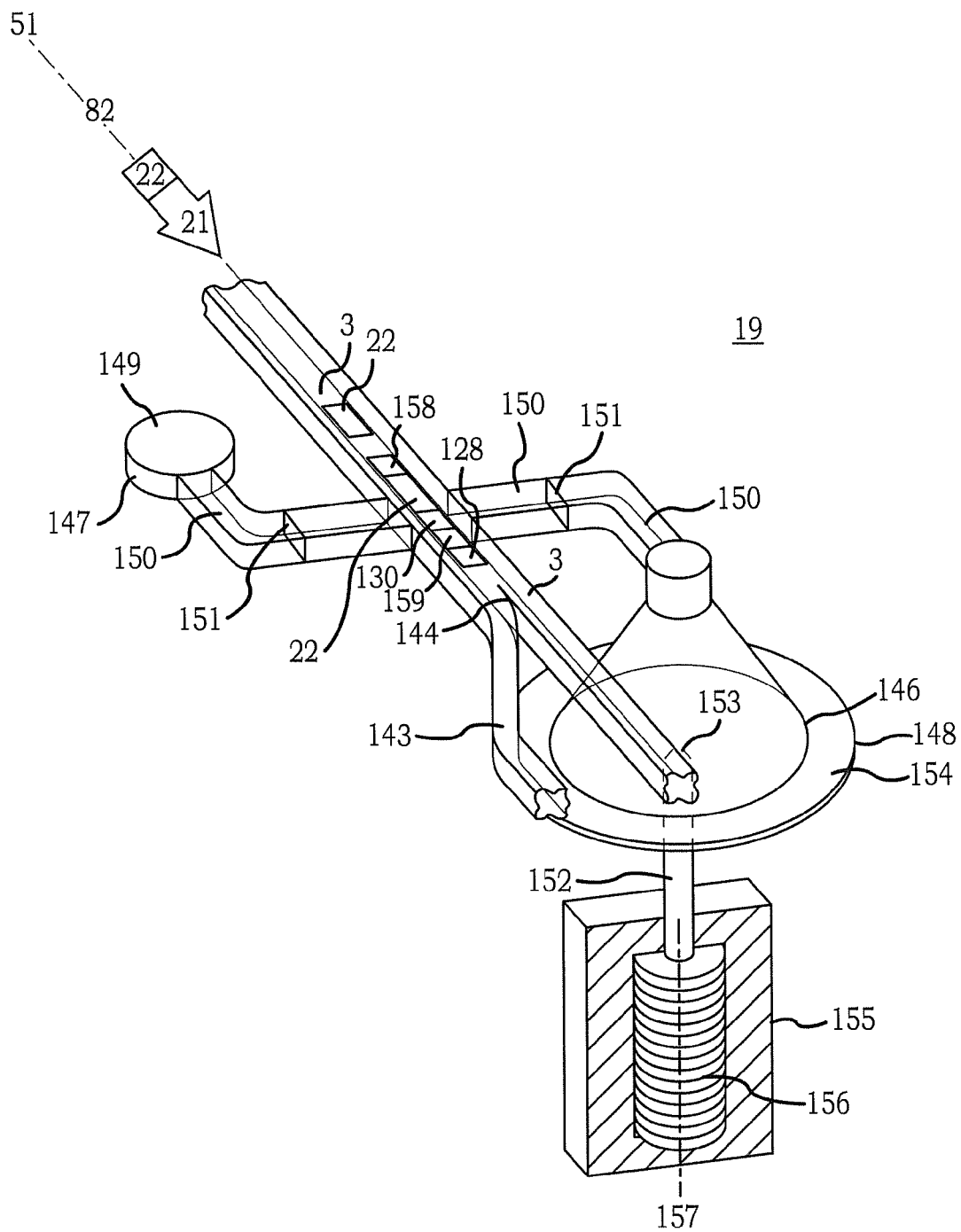
FIG. 13 is a perspective view of an embodiment of a particle sorter in the particle selection region of a particular embodiment of a flow channel of a multiple flow channel microfluidic chip.

Now referring primarily to FIG. 13, embodiments of the microfluidic chip (2) as to each of the plurality of flow channels (3) can further include a particle selection region (27) which provides the elements of a particle sorter (19). A particular embodiment of a particle sorter (19) includes a particle separation channel (143) in substantially the same plane of the microfluidic chip (2) as the corresponding flow channel (3) which first branches outwardly at an angle from the flow channel (3) and then follows the direction of the flow channel (3) in substantially parallel relation to dispose the channel (3) and the particle separation channel (143) a distance apart in range of about 50 [tm to about 100 lam. The angle at which the particle separation channel (143) diverges from the flow channel (3) can be about 45 degrees as shown in FIG. 13; however, the invention is not so limited and embodiments of the particle selection region (27) can include a particle separation channel (143) which diverges from the flow channel (3) at an angle sufficient to separate a subpopulation of particles (144) from the plurality of particles (22) within the sample fluid stream (30) and can typically be in a range of about 25 degrees and about 60 degrees. The cross-sectional area of the flow channel (3) and the particle separation channel (143) at the branch point (144) can be about one half the cross-sectional area upstream of the branch point (144). The flow channel (3) and the particle separation channel (143) each receive about one half of the volume of the sample fluid stream (30) within the flow channel (3) upstream of the branch point (144). That portion of the sample fluid stream (30) proximate the side on which the particle separation channel (143) branches continues to flow within the particle separation channel (143) and that portion of the sample fluid stream (30) proximate the side of the flow channel (3) opposite the branch point (144) of the particle separation channel (143) continues to flow within the flow channel (3). The plurality of particles (22) entrained in the sample fluid stream (30) proximate the side on which the particle separation channel (143) branches flow into the particle separation channel (143) and particles (22) entrained in the sample fluid stream (30) proximate the side opposite the branch point (144) of the particle separation channel (143) remain in the flow channel (3).

Upstream of the branch point (144) of the particle separation channel (143) the particle sorter (19) further includes a particle displacement channel (145) coupled in transverse relation to said flow channel (3) having a length disposed between a first end (146) and a second end (147) disposed on opposed sides of the flow channel (3) with first end (146) closed by a flexible membrane (148) and the second end (147) closed by a rigid terminal (149) of fixed volume. Each of the first end (146) and second end (147) of the particle displacement channel (143) contains an amount of gas (150) against which a portion of the sample fluid stream (30) from the corresponding flow channel (3) advances until compression of the amount of gas (150) results in sufficient pressure to offset further advancement of the sample fluid stream (30) within the corresponding flow path of the particle displacement channel (143). If the fluid stream (30) within particle displacement channel (143) has a substantially constant pressure, the location of the gas liquid interface (151) proximate the first end (146) and the second end (147) of the particle displacement channel (143) can depend upon change in pressure of the amount of gas (150) within the first end (146) and the second end (147) of the particle displacement channel (143). Flexure of the flexible membrane (149) which closes the first end (146) of the particle displacement channel (143) acts to correspondingly increase or decrease the volume in which the amount of gas (150) within the first end (146) of the particle separation channel (143) resides. Correspondingly, the gas pressure (150) increases or decreases within the first end (146) of the particle displacement channel (143) and the sample fluid stream (30) within the first end (146) of the particle displacement channel (143) correspondingly advances or retreats. The particle displacement channel (143) proximate the first end (146) closed by the flexible membrane (148) can have a cross-sectional area sufficiently greater than that portion of the particle displacement channel (143) distal the first end (146) such that only slight flexure of the flexibly membrane (148) can result in substantial displacement of the sample fluid stream (30) within the first end (146) of the particle displacement channel (143).

Particular embodiments of the particle sorter (19) can further provide a substantially linear pin (152) having a first pin end (153) which contacts the resiliently flexible membrane (148) on a first membrane side (154) external to the particle displacement channel (143) substantially on center. The pin (152) can travel a distance between an actuated condition and an unactuated condition to generate a corresponding amount of flexure in the flexible membrane (148). With respect to one embodiment, the pin (152) travels a distance of about 10 µm between the unactuated condition and the actuated condition generating only slight inward flexure of the flexible membrane (148) but generating a corresponding displacement of the sample fluid stream (30) within the particle displacement channel (143) of about 80 µm. The pin (152) can then travel in the opposite direction a distance of about 10 lam from the actuated condition to the unactuated condition to generate a corresponding displacement of the sample fluid stream (30) in the particle displacement channel (143) in the opposite direction of about 80 µm. The operating cycle of the pin (152) between the unactuated condition and the actuated condition and back to the unactuated condition (advance the pin 10 µm and return the pin 10 µm) can occur in a period of time in the range of between 100 microseconds to about 1000 microseconds and the operational cycle can be driven at a rate in the range of 0 cycles and about 10,000 cycles per second as required by the application. The particle sorter (19) of each of the plurality of flow channels (3) can operate at a different operating cycle rates.

Certain embodiments of the invention can perform the operating cycle at a rate selected from the group consisting of between zero and about 2000 cycles per second, between about 1,000 and about 3,000 cycles per second, between about 2,000 and about 4,000 cycles per second, between about 3,000 and about 5,000 cycles per second, between about 4,000 and about 6,000 cycles per second, between about 5,000 and about 7,000 cycles per second, between about 6,000 and about 8,000 cycles per second, between about 7,000 and about 9,000 cycles per second, between about 8,000 and about 10,000 cycles per second, or even a greater number of cycles per second.

As an illustrative non-limiting example, a microfluidic chip (2) having ten flow channels (3) each with a particle sorter (19) operating at 10,000 cycles per second in each of the ten flow channels (3) can have a combined rate of 100,000 cycles per second over the ten flow channels (3).

Again referring to FIG. 13, the operational cycle period and operational cycle rate of the pin (152) can be achieved for example by use of a piezoelectric stack actuator (155) engaged with the second pin end (156) of the pin (152). A suitable piezoelectric stack actuator (155) can be produced by stacking a plurality of piezoelectric wafers (156) or discs, which are individually contacted electrically. The piezoelectric stack axis (157) comprises the axis of linear motion. The thickness of the stack of piezoelectric wafers (156) increases by applying a voltage and thereby the total piezoelectric stack acutator (155) lengthens. Reversing voltage results in a decrease in piezoelectric stack actuator (155) length. A non-limiting example suitable for use in an embodiment of the invention, provides a piezoelectric stack actuator (155) comprised of eight generally circular piezoelectric wafers (156) each about 1 mm thick and about 2 mm in diameter. Application of voltage to this embodiment of the piezoelectric stack actuator (155) can result in an increase in length of the piezoelectric stack actuator (155) in a range of about 8 lam to about 18 lam adjustable by increasing or decreasing the voltage across the piezoelectric material. Voltage can be applied and reversed to achieve an operation cycle of between about 100 microseconds to about 1000 microseconds (or even shorter than 100 microseconds) and the operational cycle can be driven at a rate in the range of 0 cycles and about 10,000 cycles per second as required by the application. The piezoelectric stack actuator (155) provides one embodiment by which the flexible membrane (148) can be acted on; however, other devices can be used to act on the membrane resulting in deflection of a portion of the fluid stream (21) to displace a particle toward the separation channel (143), as above described, such as mechanical, electromagnetic or optical means. As one example, a microelectromechanical electrostatic displacement device with sufficient stroke, precision, and force may be coupled to the membrane to actuate the flexible membrane (148), or as a second example, the flexible membrane (148) can operate as part of a voice coil being responsive to changes in a coil's polar orientation within a magnetic field.

As each of the plurality of particles (22) pass through the detection region (26) of each of the plurality of flow channels (3) the presence or absence of one or more particle characteristics (158) can be determined based upon the bandwidth and amplitude of the side scatter (95) and emitted light (96). For example, a particle having a surface antigen (159) which binds an antibody (130) labeled with the fluorophore (128) FITC can upon interrogation by the light beam (7) emit light (96)(fluorescent light) having a peak fluorescence emission at 530 nm. Particles (22) lacking that surface antigen (159) will not upon interrogation by the light beam (7) produce emitted light (96) above background. The particle velocity (49) of each of a subpopulation of particles (160) which have the surface antigen (159) can be determined within the detection region (26) of each of the plurality of flow channels (3) as above described and the occurrence of each of the subpopulation of particles (160) at the intersection of the particle displacement channel (143) with the flow channel (3) can be timed such that actuation of an operational cycle of the pin (152) can commence as each of the subpopulation of particles (160) passes the intersection resulting in a sufficient perpendicular pulse in the sample fluid stream (30) to deflect each of the subpopulation of particles 160) to one side of the flow channel (3) upstream of the branch point (144) of the particle separation channel (143). Each of the subpopulation of particles (160) deflected toward the side of the flow channel (3) from which the particle separation channel (143) branches flow into the particle separation channel (143) while each of the plurality of particles (22) toward the side of the flow channel (3) opposite the branch point (144) remain in the flow channel (3). In certain embodiments of the invention, each of the plurality of flow channels (3) in a microflidic chip (2) can analyze particles at a rate of between 0 and 100,000 particles per second per flow channel (or even greater) and separate particles having the particle characteristics (158) of interest at a rate of 0 to 10,000 particles per second per channel (or even greater) as above described. Additional working examples are described below.

The subpopulation of particles (160) separated by deflection into the particle separation channel (143) on the basis of presence or absence of a one or more particle characteristics (158) can have a purity (161) calculated as the proportion of particles (22) in the subpopulation of particles (160) having the particle characteristic(s) (158) of interest as compared to the total number of particles (22) in the subpopulation of particles (160). A purity (161) of the subpopulations of particles (160) can achieved in the range of between about 70 percent and about 100 percent. Certain embodiments can achieve a purity (161) of the subpopulation of particles (160) selected from the group consisting of about 70% to about 80%, about 75% to about 85%, about 80% to about 90%, about 85% and about 95%, about 90% and about 100%, about 95% and about 100%, and about 100%.

The purity (161) between a plurality of subpopulations of particles (160) may vary depending on the size, shape, motility, uniformity of label, particle characteristic(s) (158) which affords the basis for the differentiation of the subpopulation of particles (160), or the like. As an example, sperm cells can be both asymmetrical and motile which can make differentiation based on small differences in emitted light (96) and separation by deflection particularly difficult as the apparent emittance and degree of deflection can vary depending upon the orientation of the sperm cell in the flow channel (3). In addressing this a relatively large number of sperm cells can be analyzed and a relatively small portion having relatively high emittance (96) can be separated as above described into a subpopulation of particles (5) being substantially all X-chromosome bearing sperm cells or bearing substantially all Y-chromosome bearing sperm cells. The DNA of X-chromosome bearing cells bearing a greater amount of fluorophore than Y-chromosome bearing sperm cells be the basis of the separation.

Now referring primarily to FIGS. 1, 2A, 3A, 4A and 5, embodiments of the microfluidic chip (2) can further include a collection region (28). As to particular embodiments of the invention each of the plurality of flow channels (3) can be directed to a common collection container (162), at least one collection container (162), or each of the plurality of flow channels (3) can be directed to a corresponding one of a plurality of collection containers (162). In certain embodiments of the invention, the plurality of particles (22) within each of the plurality of channels (3) sorted into a corresponding subpopulation of particles (160) based upon one or more particle characteristics (158) as above-described can be directed to and isolated in at least one subpopulation collection container (163) or each of the particle separation channels (143) to a corresponding one of a plurality of subpopulation collection containers (163).

As shown by the non-limiting example of FIGS. 2A, 3A, 4A, and 5A, the particle separation channels (143) of the plurality of flow channels (3) can be configured to each egress at a side (164) of the microfluidic chip (2) in a corresponding plurality of outlet elements (165). A first end (166) of a flexible collection conduit (167) can be insertingly received by each one of the plurality of outlet elements (168) and a second end (169) of the collection conduit (167) can be configured to locate within a corresponding one of the plurality of subpopulation collection containers (162). As shown by the non-limiting example of FIG. 5A.

The particles (22) which remain in each of the plurality of flow channels (3) (not delivered to the particle separation channel (143)) can be similarly delivered to individual outlets (168) as above described for delivery to a corresponding plurality of collection containers (162) or be delivered to a collection container (162) in common, or returned to the inlet region (24) of the corresponding plurality of channels (3) for reanalysis and resorting. As to other embodiments of the invention, a plurality flow channels (3) can terminate in a common collection channel (162) having a corresponding outlet element (168) which directs the plurality of particles (22) which are collected in common to a single collection container (162); however, the invention is not so limited.

Example 1. Sorting of Live CD3 Positive T-Cells

The simultaneous analysis of live CD3 positive human lymphocytes in eight separate channels of a microfluidic chip was performed for the purpose of down stream sorting of mouse PE-conjugated anti-human CD3 labeled human lymphocytes from unlabeled cells, and waste particles.

A cell mixture containing human lymphocytes and monocytes were purchased from AllCells, 5858 Horton Street, Suite 360, Emeryville, Calif. 94608 ("test cells"). The test cells ($5\times10^8$ cells per tube) having 95% viability were pelleted by centrifugation, the supernatant decanted and re-suspended in 500 µL phosphate buffered saline (800 g NaCl, 20 g KCl, 144 g $Na_2HPO_4$ and 24 g $KH_2PO_4$ in 8 L of distilled water), 0.5% bovine serum albumin, and 2 mM ethylene-diamine-tetra-acetic acid ("EDTA"). A 100 µL aliquot of PE-conjugated mouse anti-human CD3 obtained from eBioscience, 10255 Science Center Drive, San Diego, Calif. 92121 was added to the re-suspended test cells and the mixture was incubated at room temperature for 75 minutes to which 50 mL RPMI 1640, 0.5% fetal bovine serum ("FBS") culture media was added (RPMI 1640 available from Invtrogen, 1600 Faraday Avenue, Carlsbad, Calif. 92008) ("RPMI"). The test cells were pelleted by centrifugation and the supernatant decanted. The test cells were re-suspended in 10 mL RPMI and 800 µL aliquot was transferred to a fresh tube and diluted with 40 mL RPMI resulting in a concentration of $1.6\times10^6$ test cells per mL including a mixture of mouse anti-human CD3-PE antibody labeled lymphocytes ("CD3-PE positive cells") and unlabeled lymphocytes ("CD3-PE negative cells") and unlabeled monocytes ("monocytes") and particulate waste (dead cells, fragments of cells, or the like)(the "test sample").

A sheath fluid source containing RPMI and 0.5% FBS sheath fluid was pressured with nitrogen gas at about 11 psi to achieve a simultaneous flow of sheath fluid in eight channels of a multiple channel microfluidic chip, as above described. The test sample was introduced by simultaneous aspiration into each of the eight channels to establish an event rate (number of test cells per second interrogated by a laser beam at a wavelength of 532 nm in the detection region of each channel) in the range of about 160-280 test cells per second. See FIG. 14A which for each of the eight channels provides a sorter plot of the events/second for each of the eight channels. Each test cell was interrogated at by a laser beam at 532 nm upon alignment with each of the first aperture and the second aperture in the optical mask, as above described producing four separate optical threshold events upon ingress and egress from each of two apertures. If the criterion for each of the four threshold events was satisfied by a test cell, a threshold event was counted for that test cell. In each of the eight channels, 96% of the events satisfactorily met the threshold crossing conditions at the interrogation point in the detection region. See FIG. 14B which for all of eight channels a composite status plot of the number of threshold events. The velocity of the test cells in each channel was established in a range of about 1.6-1.7 meters per second. See FIG. 14C which as a composite of all eight channels shows a velocity plot of the test cells. Optical extinction signal was gated to separate the optical extinction signal for lymphocytes, monocytes and particulate waste as shown by the optical extinction plot of FIG. 14D. Emitted fluorescent light of each threshold event was received by a R5900 photomultiplier tube operating at 900 volts and the analog signal of each event was integrated over 80 µs. Fluorescence was normalized against a RCP-60-50-3 lot# AA01 calibration particle obtained from Sperotech, Inc., 27845 Irma Lee Circle, Unit 101, Lake Forest, Ill. 60045. Optical fluorescence was gated to provide a composite of all eight channels for threshold and non-threshold events as shown by the fluorescence plot of FIG. 14E and optical fluorescence was also gated to separate the optical fluorescence for lymphocytes, monocytes and particulate waste as a composite of all threshold and non-threshold events of all eight channels, as shown by the two-dimensional fluorescence plot of FIG. 14 F.

Figure 15:
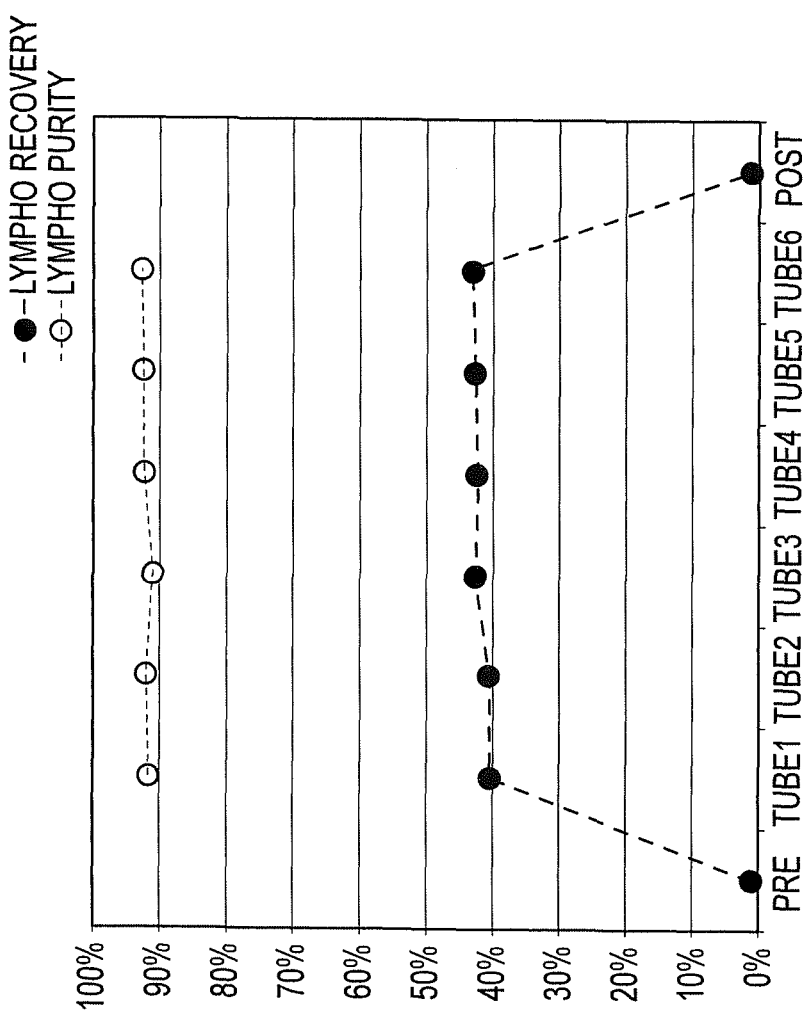
FIG. 15 is a graph which plots percentage recovery and percentage purity of CD-3-PE positive cells sorted into a subpopulation of enriched purity over elapse of time in minutes utilizing an embodiment of the particle sorter shown in FIG. 13.

Now referring to FIG. 15, CD3-PE positive cells were sorted away from CD3-PE negative cells, monocytes, and particulate waste, as above described, into a subpopulation of purified CD3-PE positive cells. The purified subpopulation of CD3-PE positive cells represent an average recovery of 41% with a purity of 92%. See FIG. 15 which separately plots percentage recovery and purity over a number of sort samples obtained during a two hour sort run including pre- and post-sort (when sorting is disabled) analysis showing an expected 0% in the active sort fluid path.

Example 2. Uniformity of Threshold Event Rate Between Flow Channels

Figure 16:
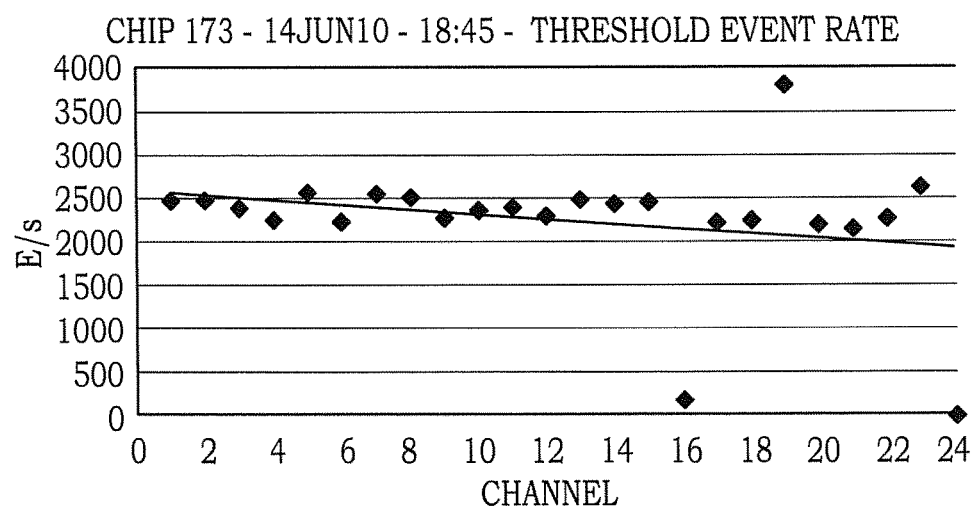
FIG. 16 is a graph which plots particle threshold event rate in relation to each of a plurality of flow channels of an embodiment of a multiple flow channel microfluidic chip.

Now referring to FIG. 16, 5 µm particles (PPX-50-50, Sperotech, Inc., 27845 Irma Lee Circle, Unit 101, Lake Forest, Ill. 60045)(also referred to as "particle sample") were analyzed using a microfluidic chip having 24 flow channels to investigate threshold event and flow rate uniformity across the plurality of flow channels. The particle concentration in the sample fluid was adjusted to $5\times10^6$ particles/mL. Pressure was adjusted within the sample source to obtain a mean sample fluid stream flow rate within each of the plurality of flow channels to achieve about 2300 threshold events per second. Substantial uniformity was observed across most of the plurality of flow channels with little variation about the mean apart from three outliers in flow channels 16, 19, and 24.

Example 3. Uniformity of Particle Velocity Between Flow Channels

Figure 17:
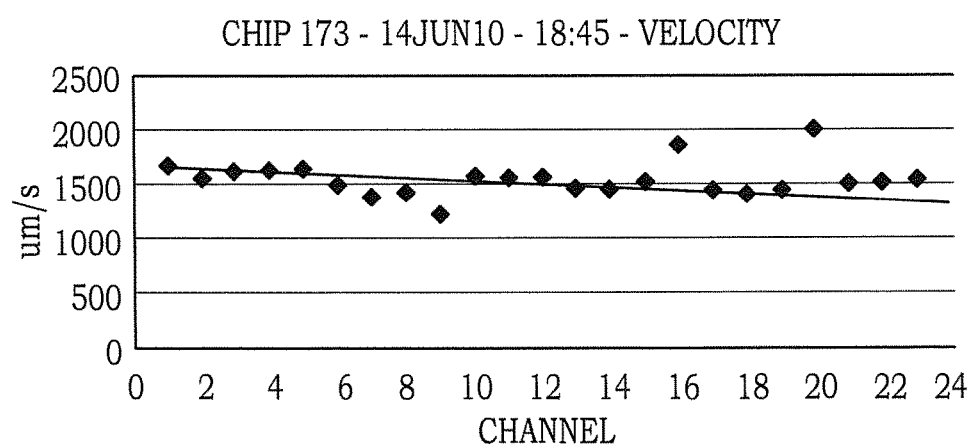
FIG. 17 is a graph which plots particle velocity in relation to each of the plurality of flow channels of the embodiment of the multiple flow channel microfluidic chip of FIG. 16.

Now referring to FIG. 17, utilizing the same microfluidic chip as in Example 2, the mean particle velocity was determined for the same particle sample as in Example 2. As shown by the data in FIG. 17, the mean particle velocity was substantially consistent across all 24 flow channels with little variation about the mean.

Example 4. Analysis of a Mixed Population of Different Particles

Figure 20:
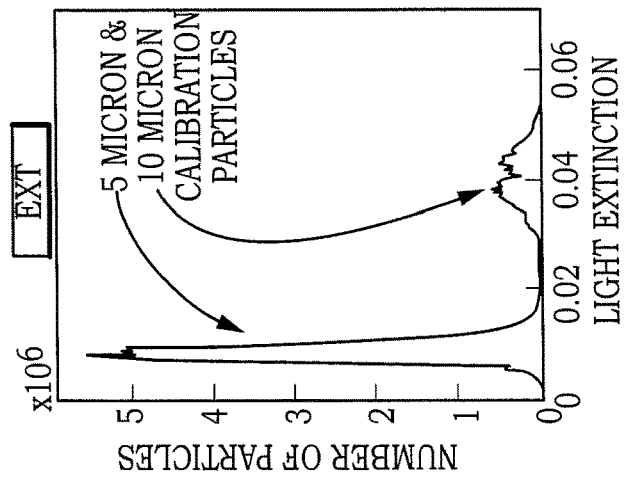
FIG. 20 is a graph which plots the combined data for light extinction for all of the plurality of flow channels of the embodiment of a multiple flow channel microfluidic chip of FIG. 18.
Figure 19:
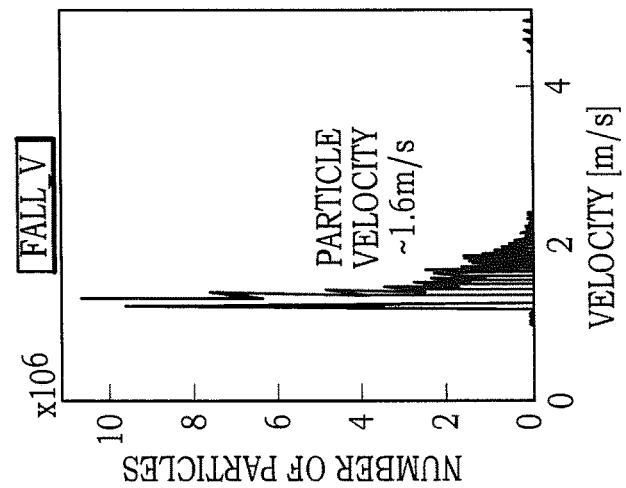
FIG. 19 is a graph which plots the combined data for particle velocity for all of the plurality of flow channels of the embodiment of a multiple flow channel microfluidic chip of FIG. 18.
Figure 18:
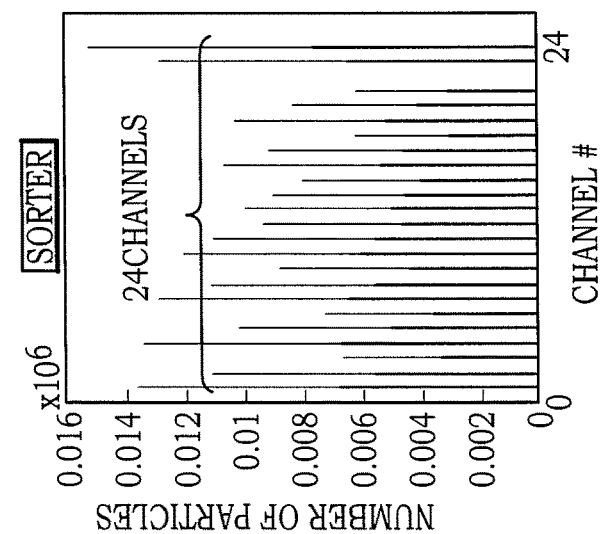
FIG. 18 is a graph which plots particle threshold event rates in relation to each of a plurality of flow channels of an embodiment of a multiple flow channel microfluidic chip.

Now referring to FIGS. 18-20, analysis of mixed population of different particles in the same sample fluid stream across 24 flow channels is demonstrated. A microfluidic chip having 24 flow channels was used for the concurrent analysis of a mixed population of 5 µm and 10 µm calibration particles (PPX-50-50, PPX-100-50, Sperotech, Inc., 27845 Irma Lee Circle, Unit 101, Lake Forest, Ill. 60045)(also referred to as the "mixed particle sample"). The population of 5 µm particles had substantially less variation in size than the 10 µm population of particles.

Now referring to FIG. 18, the mixed particle sample concentration in the sample fluid was adjusted to $5\times10^6$ particles/mL. Pressure was adjusted within the sample source to obtain a mean sample fluid stream flow rate within each of the plurality of flow channels to achieve between about 1000 and about 3000 threshold events per second per flow channel with the exception of one outliers in flow channel 22.

Now referring to FIG. 19, a particle velocity histogram combines the results of all twenty four flow channels and demonstrates a mean particle velocity of about 1.6 m/s.

Now referring to FIG. 20, light extinction data in histogram form combines the results of all twenty four flow channels and demonstrates that a mixed population of two substantially different particle types can be entrained in each of a plurality of sample fluid streams having sufficient inter-particle spacing to be readily differentiated. As shown by the light extinction data of FIG. 20 sufficient inter-particle spacing occurs between the 5 µm and 10 µm particles in each of the sample fluid streams of each of 24 flow channels (except for flow channel 22 in which no particles were interrogated) to allow each subpopulation to be individually analyzed and differentiated by the differences in light extinction.

Figure 21:
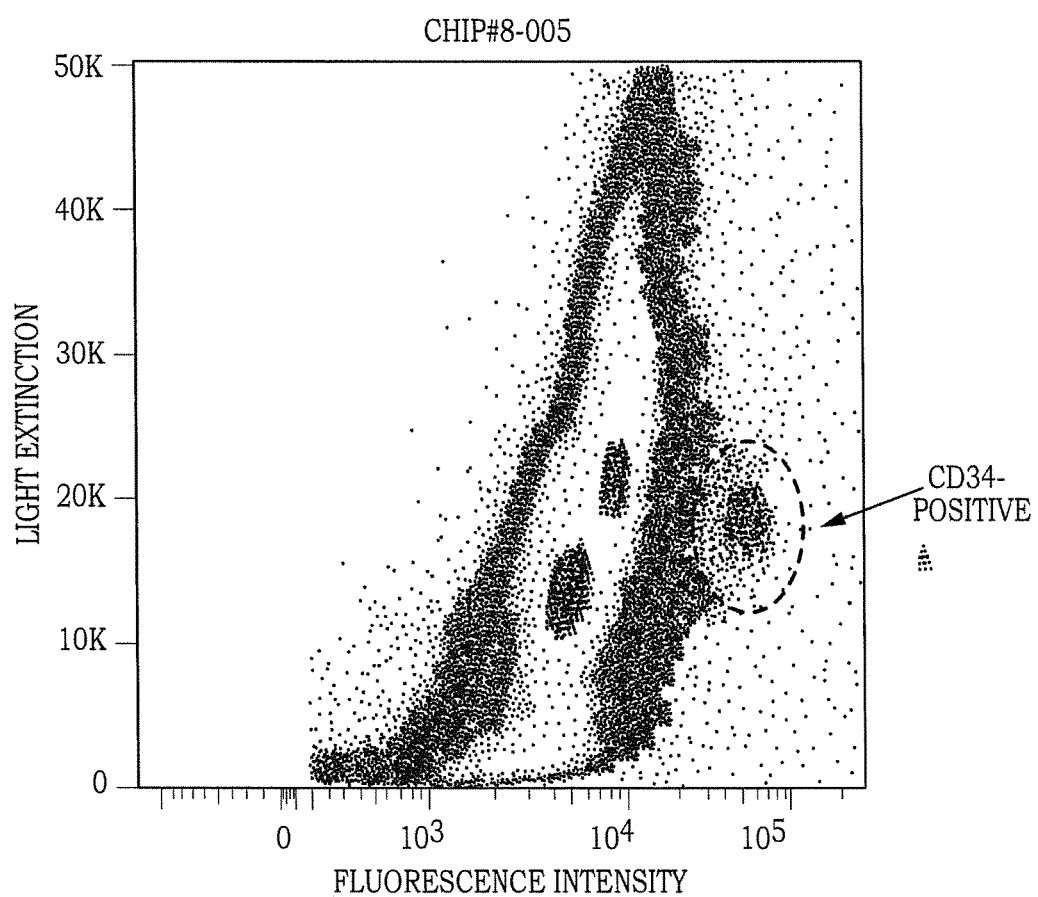
FIG. 21 is a bivariate plot of light extinction in relation to fluorescence intensity of the combined results of concurrent analysis of live CD34 positive human leukocytes in each of a plurality of flow channels of a microfluidic chip.

Example 5. Analysis of a Mixed Population of CD34 Negative and CD34 Positive Cells Now referring to FIG. 21, bivariate plot shows the combined results of concurrent analysis of live CD34 positive human leukocytes in each of 8 flow channels of a microfluidic chip. The analysis was performed for the purpose of assessing detection resolution of a rare subpopulation of cells within a population of cells. A cell mixture of human leukocytes was purchased from AllCells, 5858 Horton Street, Suite 360, Emeryville, Calif. 94608 ("test cells"). The test cells ($5\times10^8$ cells per tube) having 95% viability were pelleted by centrifugation, the supernatant decanted and re-suspended in 500 µL, phosphate buffered saline (800 g NaCl, 20 g KCl, 144 g $Na_2HPO_4$ and 24 g $KH_2PO_4$ in 8 L of distilled water), 0.5% bovine serum albumin, and 2 mM ethylene-diamine-tetra-acetic acid ("EDTA"). A 100 µL aliquot of PE-conjugated mouse anti-human CD34 obtained from BeckmanCoulter, 11800 S.W. 147th Avenue Miami, Fla. was added to the re-suspended test cells and the mixture was incubated at room temperature for 75 minutes to which 50 mL RPMI 1640, 0.5% fetal bovine serum ("FBS") culture media was added (RPMI 1640 available from Invtrogen, 1600 Faraday Avenue, Carlsbad, Calif. 92008) ("RPMI"). The test cells were pelleted by centrifugation and the supernatant decanted. The test cells were re-suspended in 10 mL RPMI and 800 µL, aliquot was transferred to a fresh tube and diluted with 40 mL RPMI resulting in a concentration of $1.6\times10^6$ test cells per mL including a mixture of mouse anti-human CD34-PE antibody labeled leukocytes ("CD34-PE positive cells") and unlabeled leukocytes ("CD34-PE negative cells") and particulate waste (dead cells, fragments of cells, or the like)(the "test sample"). A sample fluid stream of the test sample was generated in each of the 8 flow channels. The plot shown in FIG. 21, shows the combined results of analysis of emitted fluorescence versus light extinction. The plot evidences that the rare population of CD34 positive cells can be clearly differentiated from the CD34 negative population and debris populations.

Example 6. Sorting a Subpopulation of Fluorescent Particles from a Mixed Population of Fluorescent Particles and Non-Fluorescent Particles Now referring to FIGS. 22 to 26, data is presented from particle sort studies using a mixture of non-fluorescent particles (approximately 90%) and fluorescent particles (approximately 10%) particles (5 µm non-fluorescent PPX-50-50 and 5 µm Nile Red FP5056-10 respectively Sperotech, Inc., 27845 Irma Lee Circle, Unit 101, Lake Forest, Ill.

60045). A microfluidic chip similar to that shown in FIG. 5A, was utilized having eight channels and the mixture of particles was prepared and delivered to each of the eight channels generally as described in Example 4.

The bivariate plot shown in FIG. 22, shows the combined results of analysis of emitted fluorescence versus light extinction of the two particle populations as evidenced by data clusters in the lower left (non-fluorescent particle population) and lower right (fluorescent particle population) of the light extinction versus fluorescence bivariate plot. A sort gate was positioned around the fluorescent particle population to execute the sort and trigger the sort apparatus to provide sort actuation when a particle of interest enters the sensing region. Individual flow channels that provide a flow path for particles to be analyzed may branch into a number of sorting channels. Here, a two-way branch is used to produce a waste (or non-active) and keep (active) sort path. This configuration may be reversed or expanded upon to produce a plurality of active or inactive sort channels depending on the application. In one implementation of the sort system, flow may be directed to flow into the waste channel in a natural, unaltered flow state/path. Further, active sort actuation on particles of interest may deflect desired (or undesired) particles/objects into the keep flow path. As a demonstration of the system's ability to measure population statistics on particle populations, fluid output from the multiple flow channel particle analysis system were analyzed on a commercially available flow cytometer (FAC-Scan, Becton Dickinson Immunocytometry Systems, 2350 Qume Dr, San Jose, Calif. 95131).

FIG. 21 shows a fluorescent particle concentration of 8.52% within the sample mix also containing non-fluorescent particles (the remaining 91.48%). FIG. 22 shows that in this operating state, and as expected, there are no particles entering the keep channel. While sorting is active (FIG. 23), the proportion and therefore number of desired fluorescent particles within a sort sample captured from the waste channel is depleted from 8.52% to 3.75%. During the same sort, a sample collected from the keep channel sample (FIG. 24) contains a 88.64% pure fluorescent particle population showing the system is capable of sorting.

As can be easily understood from the foregoing, the basic concepts of the present invention may be embodied in a variety of ways. The invention involves numerous and varied embodiments of multiple flow channel particle analysis system including the best mode of a multiple flow channel particle analysis structure and methods of particle analysis using such multiple flow channel particle analysis structure.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "fluid stream" should be understood to encompass disclosure of the act of "streaming a fluid"—whether explicitly discussed or not—and, conversely, were there effectively disclosure of the act of "streaming a fluid", such a disclosure should be understood to encompass disclosure of "a fluid stream" and even a "means for streaming a fluid." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

Thus the applicant(s) should be understood to claim at least: i) a multiple flow channel particle analysis structure as herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this international PCT patent specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

What is claimed is:

1. A particle analysis system comprising:
    a plurality of sample sources;
    a plurality of outlet elements;
    a microfluidic chip fluidically coupled to the plurality of sample sources and the plurality of outlet elements, the microfluidic chip including a plurality of simultaneously operating flow channels where each flow channel is fluidically coupled to one of the plurality of sample sources and a respective one of the plurality of outlet elements, the flow channels fluidically isolating samples from each of the sample sources from samples of other sample sources while traversing the microfluidic chip from the plurality of sample sources to the plurality of outlet elements, wherein each flow channel includes a detection region aligned to admit a beam of light into the detection region of the flow channel to detect a particle;
    a detector system including a plurality of detectors, each detector optically coupled to a respective flow channel in the plurality of flow channels to independently generate signals associated with the respective flow channel based on at least one of light passing through or light emitted from the flow channel; and
    an analyzer to concurrently analyze the plurality of the signals generated by the detector system to determine which particles flowing through the flow channels satisfy a preliminary criterion and concurrently analyze the signals of those particles satisfying the preliminary criterion to control operation of the particle analysis system.

2. The particle analysis system of claim 1, wherein the microfluidic chip further comprises a plurality of inlet elements, each inlet element fluidically coupled to one of the plurality of flow channels and to one of the plurality of sample sources.

3. The particle analysis system of claim 2, wherein the plurality of inlet elements are disposed in an inlet element pattern.

4. The particle analysis system of claim 3, wherein the inlet element pattern comprises spaced columns and rows.

5. The particle analysis system of claim 3, wherein the inlet element pattern comprises a linear array.

6. The particle analysis system of claim 1, wherein the plurality of sample sources includes wells in a 24-well plate or 96-well plate.

7. The particle analysis system of claim 1, wherein each outlet element in the plurality of outlet elements is fluidically coupled to one of a plurality of collection containers.

8. The particle analysis system of claim 1, wherein the system comprises at least 24 flow channels.

9. The particle analysis system of claim 1, wherein the analyzer assesses the plurality of signals at a rate in a range between 5,000 events per second and 100,000 events per second.

10. The particle analysis system of claim 1, further comprising a plurality of particle sorters, each particle sorter associated with one of the plurality of flow channels.

11. The particle analysis system of claim 1, wherein satisfaction of the preliminary criterion for any individual particle is based on the analysis of the plurality of signals generated by the detector system, at least a portion of the plurality of signals associated with one or more of a leading edge or a trailing edge of one or more optical apertures.

12. The particle analysis system of claim 1, wherein the analyzer further analyzes a plurality of signals generated by the detector system including using one or more of a light extinction signal, a light scatter signal, or an emitted light signal to assess threshold events in said plurality of flow channels and to independently trigger processing steps for individual flow channels of said plurality of flow channels.

* * * * *